US012730111B2

(12) United States Patent
Chang et al.

(10) Patent No.: US 12,730,111 B2
(45) Date of Patent: Sep. 8, 2026

(54) SYSTEMS, METHODS, AND COMPOSITIONS TO IDENTIFY NEW PROTEIN TARGETS OF A CHEMICAL COMPOUND OR ITS DERIVATIVES

(71) Applicants: Geen-Dong Chang, Taipei City (TW); Ming-Shyue Lee, Taipei City (TW); Cheng-Han Yu, Taipei City (TW)

(72) Inventors: Geen-Dong Chang, Taipei City (TW); Ming-Shyue Lee, Taipei City (TW); Cheng-Han Yu, Taipei City (TW)

( * ) Notice: Subject to any disclaimer, the term of this patent is extended or adjusted under 35 U.S.C. 154(b) by 819 days.

(21) Appl. No.: 18/067,308

(22) Filed: Dec. 16, 2022

(65) Prior Publication Data

US 2023/0118154 A1 Apr. 20, 2023

Related U.S. Application Data

(63) Continuation-in-part of application No. 16/847,206, filed on Apr. 13, 2020, now abandoned.

(60) Provisional application No. 62/835,639, filed on Apr. 18, 2019.

(51) Int. Cl.
*G01N 33/68* (2006.01)
*G01N 33/543* (2006.01)

(52) U.S. Cl.
CPC ....... *G01N 33/68* (2013.01); *G01N 33/54306* (2013.01)

(58) Field of Classification Search
None
See application file for complete search history.

(56) References Cited

PUBLICATIONS

Yu et al., "Antibody-assisted target identification reveals afatinib, an EGFR covalent inhibitor, down-regulating ribonucleotide reductase", Oncotarget, vol. 9, No. 30, pp. 21512-21529 (Year: 2018).*

Cote et al., "Generation of human monoclonal antibodies reactive with cellular antigens", Proc. Natl. Acad. Sci. USA, 1983, pp. 2026-2030, vol. 80.

Dudkin et al., "Toward a Prostate Specific Antigen-Based Prostate Cancer Diagnostic Assay: Preparation of Keyhole Limpet Hemocyanin-Conjugated Normal and Transformed Prostate Specific Antigen Fragments", J. Am. Chem. Soc. 130, 2008, pp. 13598-13607.

* cited by examiner

*Primary Examiner* — Anand U Desai
(74) *Attorney, Agent, or Firm* — MUNCY, GEISSLER, OLDS & LOWE, P.C.

(57) ABSTRACT

Systems and methods to identify new protein targets of a chemical compound or its derivatives were described. The methods can be used for detection of new binding partners as long as the chemical compound can covalently bind to the protein targets. Once protein targets are resolved, information related to new protein targets can then be used to couple with real-world patient data such as adverse events, efficacy data, and disease correlation data to deduce real-world evidence. Systems collectively with all this information can aide clinical development and use of pharmaceutical drug. Methods are provided for detection of covalently bound phenyl vinyl sulfone (PVS) or its derivatives, and afatinib or its derivatives. Furthermore, generation of antiserum recognizing carrier bound PVS or carrier bound afatinib is described. PRMT1 is described as a new target of PVS and RRM1, RRM2, and NFKB are described as new targets of afatinib.

5 Claims, 13 Drawing Sheets

(B)

(A)

Figure 8:
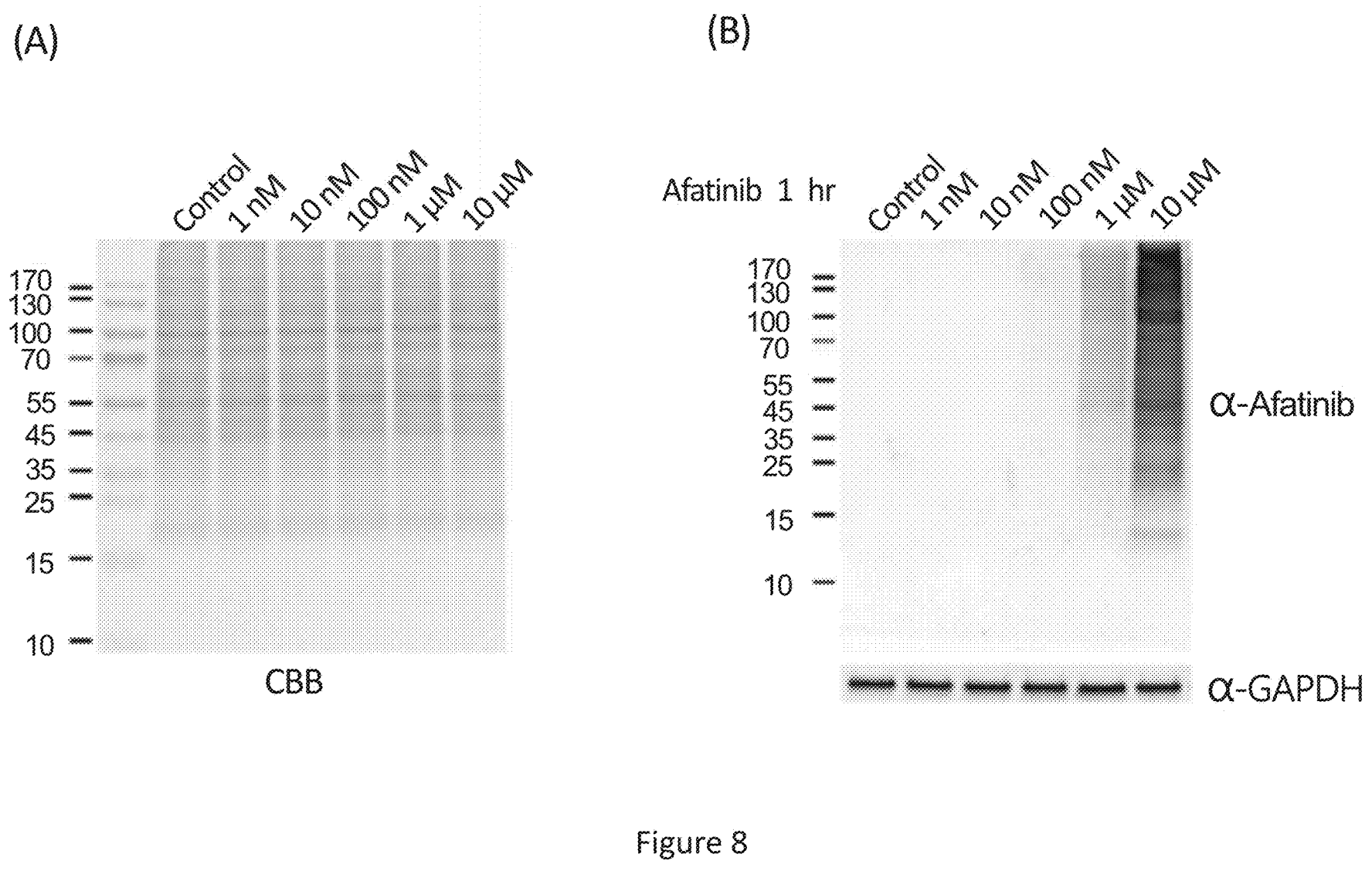

(A)

170
130
100
70
55
45
35
25
15
10

Control
1 nM
10 nM
100 nM
1 µM
10 µM

CBB (B)

Afatinib 1 hr 170
130
100
70
55
45
35
25
15
10

Control
1 nM
10 nM
100 nM
1 µM
10 µM

α-Afatinib

α-GAPDH

SYSTEMS, METHODS, AND COMPOSITIONS TO IDENTIFY NEW PROTEIN TARGETS OF A CHEMICAL COMPOUND OR ITS DERIVATIVES

CROSS REFERENCE TO RELATED APPLICATIONS

This application is a Continuation-in-Part of co-pending application Ser. No. 16/847,206, filed on 13 Apr. 2020, for which priority is claimed under 35 U.S.C. § 120, the entire contents of all of which are hereby incorporated by reference.

BACKGROUND OF THE INVENTION

1. Field of the Invention

The present disclosure generally relates to the technologies to improve understanding of novel binding targets of chemical compounds in the class of irreversible small molecule drugs. This information can be useful for the improvement of efficacy, toxicity, and dosing of existing approved usage, or the extension of medical and regulatory usage of this class of drugs.

2. Description of the Related Art

Protein tyrosine phosphorylation, dynamically controlled by the activities of protein tyrosine kinases (PTKs) and protein tyrosine phosphatases (PTPs), is critical in the regulation of cell proliferation, differentiation, metabolism and survival. Overall, there are over 100 human PTP-superfamily genes that can be classified into the classical phosphotyrosine-specific phosphatases and the dual specificity phosphatases (1). The classical PTPs possess an active-site site motif $HCX_5R$, in which the cysteine sulfhydryl group deprotonates easily due to its low pKa and functions as a nucleophile for the enzymatic catalysis (2, 3). The low pKa property of the catalytic cysteine residue also renders PTPs susceptible to oxidation and transient inactivation by reactive oxygen species (ROS). For instances, PTPN1 (PTP1B) is reversibly oxidized in response to EGFR activation (4). Similar modification of the catalytic cysteine residue has been shown for PTPN11 (SHP2) in PDGF signaling (5), PTPN1 and PTPN2 (TC-PTP) in insulin signaling (6), and PTPN6 (SHP1) in B cell receptor signaling (7, 8). In addition, SHP-1, SHP-2, and PTP1B are prone to oxidation by NO in the signaling of insulin or to ionization (9, 10). Therefore, transient burst of ROS and NO causing temporary inactivation of PTPs in response to PTK activation seems to be a general mechanism for maintaining high levels of tyrosine phosphorylation in the early phase of growth factor receptor activation.

Malfunction of both PTKs and PTPs is involved in the development of some inherited and acquired human diseases (1, 11, 12). For instance, PTP-1B has been linked to obesity and diabetes (13, 14), PTP sigma to ulcerative colitis (15) and lymphoid-specific PTP (PTPN22) to autoimmune disorders (16, 17). Therefore, potent and specific PTP inhibitors can be used to study the role of PTPs in these diseases and be eventually developed into chemotherapeutic agents. Development of small molecule drugs targeting specific PTP is challenging because the PTP members are characterized by an exceptionally high degree of sequence conservation across their active sites (18, 19). Common approaches in developing novel small molecules directed to a particular enzyme include a traditional high-throughput screen using a chemical library and in vitro enzyme assays, synthesis of derivatives based on structure-activity relationship (SAR), and optimization of affinity and selectivity. Achieving target specificity may be the ultimate aim of drug development however it requires the knowledge of all targets of the drug. A previous report (20) estimated that a drug interacted on average with 6.3 targets. Thus, target identification of small molecule compounds seems to be the bottleneck of drug development (21).

Phenyl vinyl sulfone (PVS) and phenyl vinyl sulfonate (PVSN) were characterized as a new class of mechanism-based PTP inhibitors (22). These two compounds inactivate PTPs by mimicking the phosphotyrosine structure and providing a Michael addition acceptor for the active-site cysteine residue of PTPs. Based on these observations, we attempted to develop an antiserum against PVS and use the antiserum in the identification of PVS-tagged proteins through immunoprecipitation coupled with mass spectrometry analysis. Herein, using anti-PVS antiserum as an example, we have demonstrated the applications of antiserum against a covalent inhibitor in the identification of targets of inhibitors. PVSN and Bay 11-7082, structurally similar compounds to PVS, could inhibit the glutathione reductase activity in vitro. PVS, PVSN, and Bay 11-7082 could inhibit the protein arginine methyltransferase 1 (PRMT1) activity in vitro, and treatment of cells with PVSN, Bay 11-7082, or Bay 11-7085 caused the decline of the levels of protein asymmetric dimethylarginine catalyzed by PRMT1.

Small molecule inhibitors targeting epidermal growth factor is another area covalent bound chemical compounds are explored for their pharmaceutical activities. The epidermal growth factor receptor (EGFR) is one of four members of the ErbB family along with HER2 (ErbB2), HER3 (ErbB3), and HER4 (ErbB4). Functional ErbB receptors are activated by binding to the corresponding ligands, which leads to receptor dimerization and subsequent autophosphorylation or transphosphorylation on certain tyrosine residues, commencing a signaling cascade involved in the regulation of gene expression and many cellular processes [65, 66]. Mutations or overexpression of EGFR is often found in various human cancers, including non-small-cell lung cancer (NSCLC) [67]. Erlotinib and gefitinib are the first-generation EGFR tyrosine kinase inhibitors (TKIs) with high specificity to EGFR [67]. These two drugs bind reversibly to the ATP binding pocket of the catalytic domain and effectively block the downstream signaling initiated from EGFR ligand binding. However, resistance to these drugs occurs frequently in NSCLC patients due to de novo EGFR mutations, especially deletions in exon 19 (EGFRdel19) and the exon 21 L858R mutation (EGFR L858R) [68, 69]. Afatinib developed under Boehringer Ingelheim is a covalent inhibitor of ErbB family with IC50 values of 0.5, 14, and 1 nM for EGFR, HER2, HER4 receptor, respectively [69]. Afatinib contains a Michael acceptor group rendering it covalently reactive to a specific cysteine residue within the catalytic cleft (Cys797 in EGFR, Cys805 in HER2, and Cys803 in HER4) and thus preventing the binding of ATP and kinase activation [70, 71]. As afatinib treatment in NSCLC patients significantly improved progression free survival as compared to the standard platinum-based chemotherapy in two pivotal Phase III studies [72, 73], afatinib has been approved in the US in 2014 for the first-line treatment of NSCLC patients who have EGFR mutations that potentially may cause resistance to gefitinib and erlotinib treatment. Erlotinib, gefitinib, and afatinib have also been investigated in the treatment of head and neck cancer [74-76], and afatinib in treating breast cancer [76-78].

Cellular deoxyribonucleoside triphosphates (dNTPs) pool, required for DNA replication and repair, is replenished by both salvage and de novo pathways. Ribonucleotide reductase (RNR) catalyzes the rate-limiting step of the de novo pathway converting a ribonucleoside diphosphate to the corresponding deoxyribonucleoside diphosphate. Mammalian ribonucleotide reductase consists of catalytic a (RRM1) and free radical-generating β (RRM2) subunits. The enzyme is allosterically regulated through binding of ATP, dATP, TTP or dGTP to the S site and (d)ATP binding to the A site, both in the a subunit [79]. RRM1 and RRM2 are often overexpressed in cancer tissues including lung [80]. In addition, low RRM2 mRNA expression was associated with a significantly higher response rate in patients treated with docetaxel and gemcitabine [81]. Resistance to gemcitabine has been associated with both RRM1 and RRM2 overexpression [82, 83]. Thus, ribonucleotide reductase becomes as an important target for cancer drug development.

During the development of tyrosine kinase inhibitors (TKIs), structure-based drug design, kinome profiling and cellular assays are routinely used to obtain potent and selective compounds against certain tyrosine kinases [84, 85]. Achieving target specificity may be the ultimate aim of drug development but it requires the knowledge of all targets of the drug. Drug-target network analysis estimated that a drug interacts on average with 6.3 targets [86]. Thus, target identification of small-molecule compounds seems to be the bottleneck of drug development [87]. Due to the method limitation in target identification, most TKIs are only examined among the kinase members in the understanding of inhibitor specificity. Most kinase inhibitors might not be as selective as expected because they also target the ATP-binding site of other protein kinases and other ATP-binding proteins may have ATP binding sites indistinguishable from those in protein kinases [88]. In support of this notion, afatinib reversed ABCB1-mediated multidrug resistance in ABCB1-overexpressing ovarian cancer cells by inhibiting the efflux function of ABCB1 [89] and GW8510, a cyclin-dependent kinase inhibitor, inhibited RRM2 expression through promoting its proteasomal degradation [90]. Therefore, close scrutinization of the potential targets of TKIs, especially those already in clinical use, can lead to better understanding of the binding specificity and the resulting therapeutic efficacy. Here, we offer a newly developed method to identify potential target proteins of afatinib. We raised an antiserum against afatinib, and this antiserum can recognize the afatinib-tagged proteins in the cells. Using this method, target identification by specific tagging and antibody detection (TISTA), we found that afatinib covalently bound to RNR, leading to inhibition of RNR activity, downregulation of the RNR protein level, and cell cycle perturbation in PC-9 cells (formerly known as PC-14). Interestingly, afatinib treatment repressed the upregulation of RNR protein level induced by treatment of gemcitabine. Long-term incubation of low-dose afatinib in PC-9 cells and EGFR-null Chinese hamster ovary (CHO) cells also significantly caused downregulation of RNR protein level. Thus, TISTA has been proved to be one powerful method for target identification of covalent drugs such as afatinib in drug repurposing.

SUMMARY OF THE INVENTION

Embodiments of the present disclosure include systems and methods for identification of novels targets of pharmaceutical chemical compounds. Embodiments of this disclosure include, for example, methods to generate antiserum detecting protein bound pharmaceutical chemical compounds, methods for the detections of protein-pharmaceutical chemical complexes in cell, tissue, or cellular lysate, methods of detection of novel proteins bound by pharmaceutical chemical compounds, methods to compare novel targets and patient outcome data, and methods to expand clinical testings and use of pharmaceutical chemical compound in human.

In one aspect, the present disclosure is directed to a method for detection of novel binding proteins of a pharmaceutical chemical compound or its derivatives performed using culture human cell lysates, lysates from animal cells, lysates from primary human cells or tissues, or live cultured human or animal cells. The system may include a detecting agent raised in animals as antiserum, or a monoclonal antibody obtained with known methods, or a single chain binding protein using known methods, or a combination of all previously mentioned reagents.

In another aspect, the present disclosure is directed to a system of detection of novel targets by a pharmaceutical chemical compound. Such system may include a step to generate detection agent, a step to immunoprecipitate a complex between novel protein targets and a pharmaceutical chemical compound, a step to perform aforementioned steps in an automatic manner, an analysis step to match target data and patient data, and a step to expand clinical testings or clinical use of a pharmaceutical chemical compound. This system may include a final step to explore new compound modification or design to improve efficacy, toxicity, or dosing of a pharmaceutical chemical compound.

In yet another aspect, the present disclosure is directed to a method of detection of novel protein targets of pharmaceutical compound afatinib or its derivatives.

In another aspect, the present disclosure is directed to a composition of detection of protein bound afatinib or its derivatives. This composition may be a form of antiserum, a monoclonal antibody, a single chain protein or antibody, or a combination of aforementioned reagents.

In yet another aspect, the present disclosure is directed to a method of detection of novel protein targets of compound phenyl vinyl sulfone or its derivatives.

In another aspect, the present disclosure is directed to a composition of detection of protein bound phenyl vinyl sulfone or its derivatives. This composition may be a form of antiserum, a monoclonal antibody, a single chain protein or antibody, or a combination of aforementioned reagents.

In another aspect, the present disclosure is directed to a method to treat patient with chemical compound, whereas this chemical compound is covalent bound with arginine methyltransferase 1 as a therapeutic target.

In another aspect, the present disclosure is directed to a method to treat patient with chemical compound, whereas this chemical compound is covalent bound with ribonucleotide reductase as a therapeutic target.

In another aspect, the present disclosure is directed to a method to treat patient with chemical compound, whereas this chemical compound is covalent bound with nuclear factor of kappa B (NFkB) as a therapeutic target.

In another aspect, the present disclosure is directed to a method for a detection of novel binding proteins of a pharmaceutical chemical compound or its derivatives performed with lysates from cultured human cells, comprising following steps:

(a) generating a detection agent raised by a complex of the pharmaceutical chemical compound conjugated with a protein carrier, wherein the pharmaceutical chemical compound is protein tyrosine kinase inhibitor or protein tyrosine phosphatase inhibitor; the detection agent is antiserum, single-chain variable fragment binding protein, monoclonal antibody in any immunoglobulin format, or a combination thereof, which is against the pharmaceutical chemical compound;

(b) generating cellular lysates after the pharmaceutical chemical compound treatment from cultured human cells;

(c) executing an immunoprecipitation performed with the cellular lysates and the detection agent to immunoprecipitate a complex of the pharmaceutical chemical compound and its target binding proteins;

(d) executing a proteomic analysis to identify the target binding proteins of the pharmaceutical chemical compound.

In some embodiments, the protein carrier is keyhole limpet Hemocyanin, ovalbumin or bovine serum albumin.

In some embodiments, the pharmaceutical chemical compound is protein tyrosine kinase inhibitor, which is afatinib, or its derivatives erlotinib or gefitinib.

In some embodiments, ribonucleotide reductase (RNR) is one of the target binding proteins of the pharmaceutical chemical compound.

In some embodiments, nuclear factor of kappa B (NFkB) is one of the target binding proteins of the pharmaceutical chemical compound.

In some embodiments, the pharmaceutical chemical compound is protein tyrosine phosphatase inhibitor, which is phenyl vinyl sulfone (PVS), or its derivatives phenyl vinyl sulfonate (PVSN) or Bay 11-7082.

In some embodiments, protein arginine methyltransferase 1 (PRMT1) is one of the target binding proteins of the pharmaceutical chemical compound.

It is to be understood that both the foregoing general description and the following detailed description are examples and explanatory only and are not restrictive of the disclosure embodiments as claimed.

The accompanying drawings constitute a part of this specification. The drawings illustrate several embodiments of the present disclosure and, together with the description, serve to explain the principles of the disclosure embodiments as set forth in the accompanying claims.

BRIEF DESCRIPTION OF THE DRAWINGS

For a more complete understanding of the principles disclosed herein, and the advantages thereof, reference is now made to the following descriptions taken in conjunction with the accompanying drawings.

FIG. 8 describes example of afatinib as a covalent protein tyrosine kinase inhibitor (TKI). PC9 cells were treated with various concentrations of afatinib in PBS for 1 h, washed with PBS for three times, and lysed with RIPA lysis buffer containing 10 mM 1,4-dithioerythritol. The proteins in the lysate were examined by Coomassie blue G-250 staining (left panel), and anti-afatinib (right panel) following SDS-PAGE and electrotransfer. The control groups were treated with the same volume of DMSO. CBB: Coomassie blue G-250, α-pY: anti-phosphotyrosine. The drawing is in accordance with various embodiments.

GAPDH gene expression level, recognized by anti-GAPDH antibody (α-GAPDH) is served as a control. Panel (B) indicates level of EGFR, ribonucleotide reductase 1 (RRM1), and ribonucleotide reductase 2 (RRM2) in a co-precipitation experiment using anti-afatinib antiserum as a pull-down agent.

Figure 10:
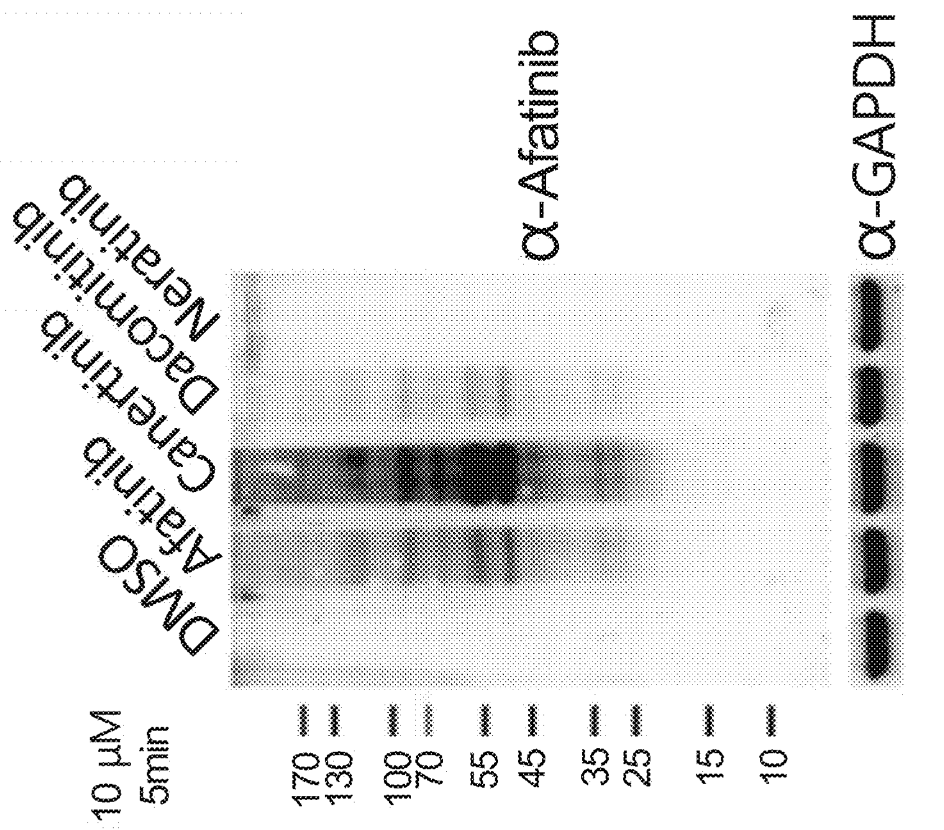

FIG. 10 shows recognition of covalent binding complexes of afatinib, canertinib, and dacomitinib, but not neratinib by anti-afatinib antiserum.

Figure 11:
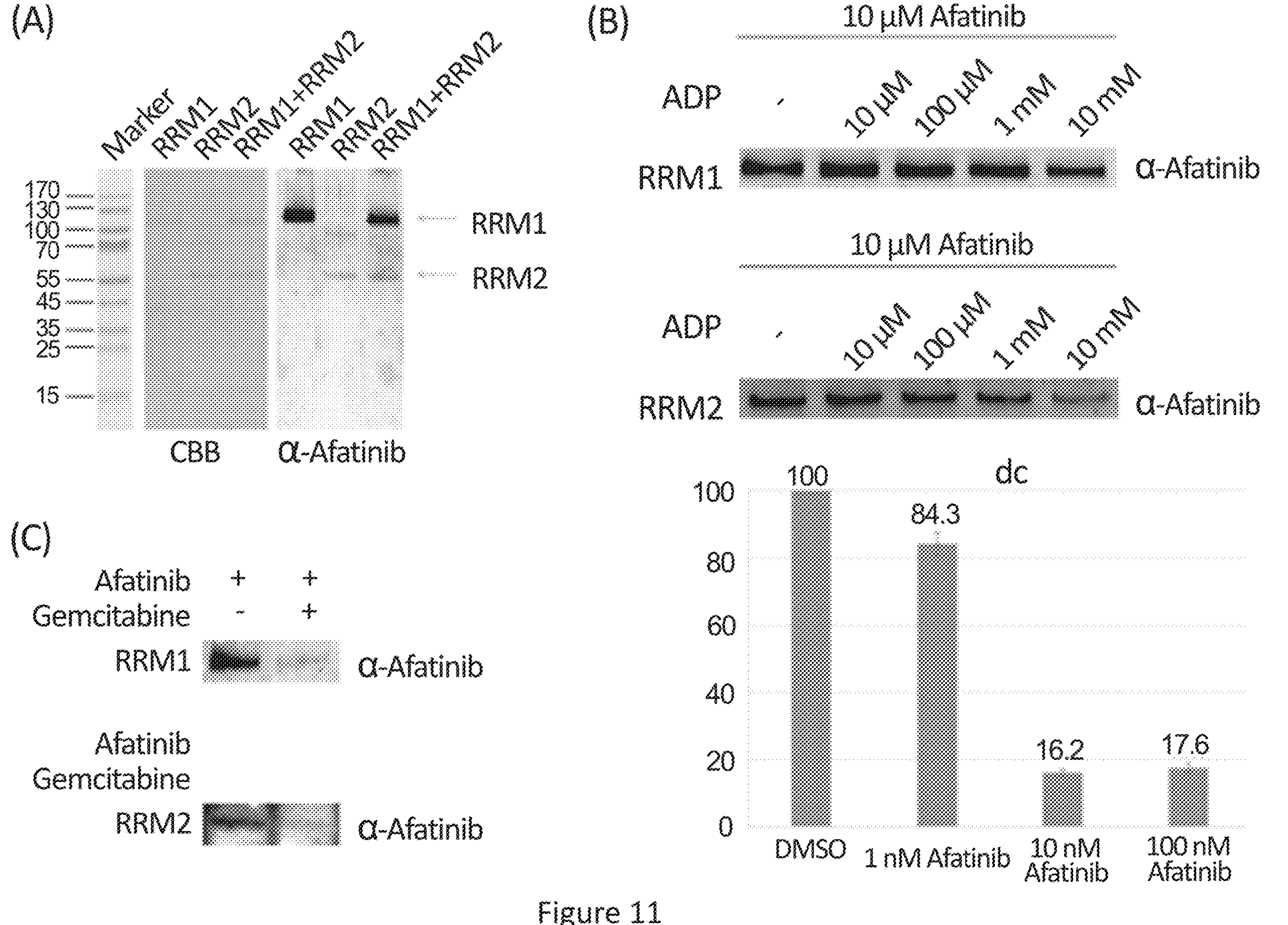

FIG. 11 indicates examples of ribonucleotide reductase as a direct target of afatinib. (A) The reaction mixture contained 2 μg recombinant RRM1 or/and 1 μg RRM2 in the presence of 12.5 μM afatinib for 1 h at 37° C. The protein concentration was about 0.25 μM. The reaction product was examined by Coomassie blue G-250 staining and immunoblotting with anti-afatinib antiserum (α-Afatinib). (B) The reaction mixture initially contained 1 μg recombinant RRM1 or RRM2 in the presence of various concentrations of ADP. After incubation for 15 min, the reaction solution was added with afatinib to a final concentration of 10 μM. The reaction was further incubated at 37° C. for 1 h, and then the reaction product was examined by SDS-PAGE and immunoblotting with anti-afatinib antiserum (α-Afatinib). (C) The reaction mixture initially contained 1 μg recombinant RRM1 or RRM2 in the presence of 2.5 mM gemcitabine. After incubation for 15 min, the reaction solution was added with afatinib to a final concentration of 10 μM. The reaction was further incubated at 37° C. for 30 min, and then the reaction product was examined by SDS-PAGE and immunoblotting with anti-afatinib antiserum (α-Afatinib). (D) Rapidly growing PC-9 cells were lysed by freezing and thawing. The cell lysate was treated with afatinib for 1 h and then ribonucleotide reductase activity was measured with the addition of a reagent mixture containing ATP and CDP for 1 h. The reaction product dCDP was extracted from the lysate and treated with alkaline phosphatase. The digested product deoxycytidine was measured with LC-MS analysis.

Figure 12:
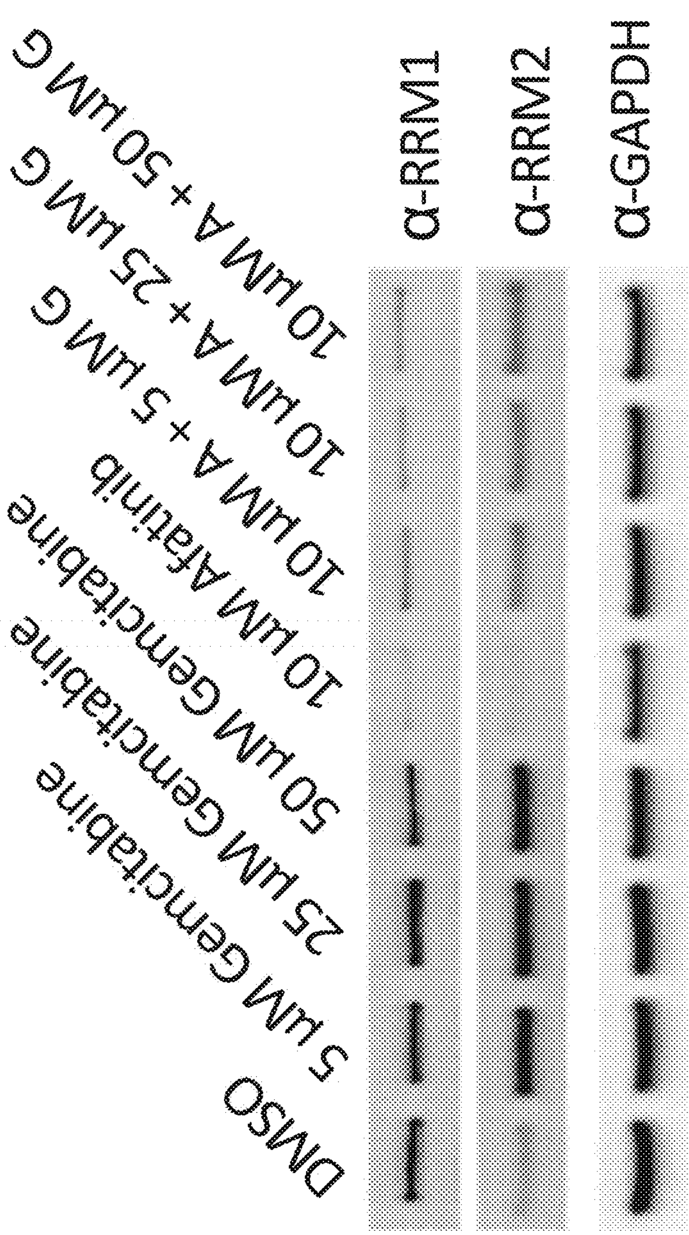

FIG. 12 indicates effect of combination treatment of afatinib and gemcitabine in PC9 cells. PC9 cells were treated with various concentrations of gemcitabine in the presence or absence of 10 μM afatinib in cultured medium containing FBS for 24 h. After the treatment, the cells were washed with PBS for three times and then lysed with urea lysis buffer containing 1 μM cysteine. The cell lysate was examined by immunoblotting with anti-RRM1 antibody (α-RRM1) and anti-RRM2 antibody (α-RRM2) following SDS-PAGE.

Figure 13:
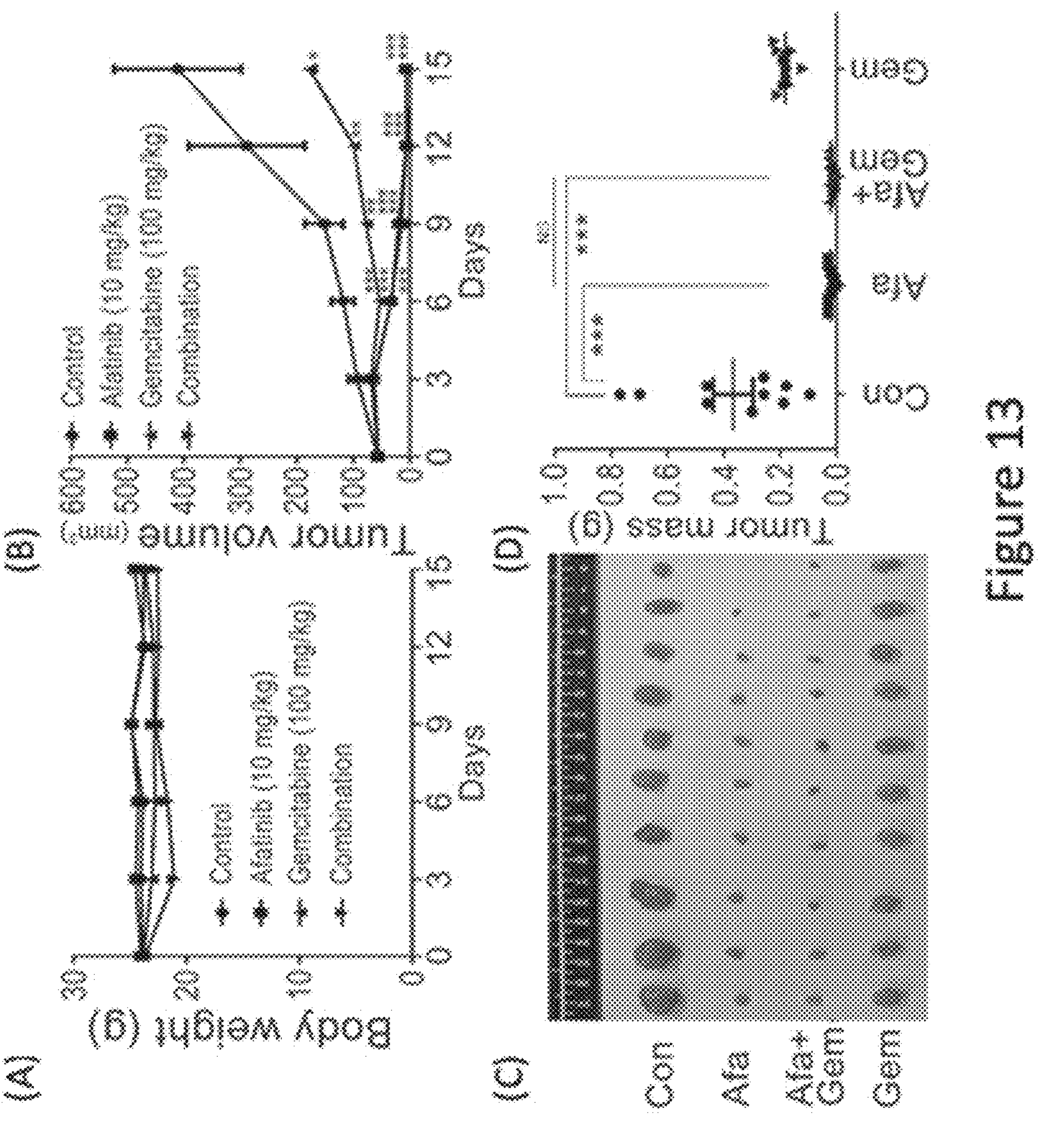

FIG. 13 shows example of in vivo combination effect of afatinib and gemcitabine in mice. Animal body weights are shown in panel (A). And tumor volumes are shown in panel (B). Panels (C) and (D) show tumor mass analysis. Fifteen days after the treatment, the mice were sacrificed and the tumor lesions were taken out, weighed and photographed. The mouse numbers for each group were 10 (n=10) and one tumor lesion was vanishing after the afatinib treatment in the group. The tumor masses were statistically calculated and plotted. (*: $p<0.05$, : $p<0.01$, and *: $p<0.001$).

DETAILED DESCRIPTION OF THE INVENTION

Embodiments of systems and methods for detecting gene fusions are described and illustrated herein.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Harlow and Lane, Using Antibodies: A Laboratory Manual (Second ed., Cold Spring Harbor Laboratory Press, Cold Spring Harbor, N.Y. 1999). The nomenclatures utilized in connection with, and the laboratory procedures and techniques described herein are those well-known and commonly used in the art.

In various embodiments, a "system" sets forth a set of components, real or abstract, comprising a whole where each component interacts with or is related to at least one other component within the whole.

In various embodiments, a "small molecule chemical compound", or a "small molecule compound", or a "chemical compound", may refer to any molecule that is produced synthetically in laboratory by a person, or naturally by a biological organism such as primary metabolites, secondary metabolites, and other natural compounds, excluding large polymeric molecules such as proteins, polysaccharides, lipids, and nucleic acids (DNA and RNA).

In various embodiments, the phrase "sequencing run" refers to any step or portion of a sequencing experiment performed to determine some information relating to at least one biomolecule (e.g., peptide molecule).

In various embodiments, the phase a "gene", or a "protein", or a "peptide", or a "polypeptide", or an "enzyme" refers to a representation of a gene and its functional protein or functional enzyme deduced by the DNA (deoxyribonucleic acid) in the human genome, whose notion is well known in the art and as described in various general and specific references.

In various embodiments, a "structural variant" refers to a variation in the structure of a chromosome. Structural variants can include deletions, duplications, copy-number variants, insertions, gene fusions, inversions and translocations. Many of structural variants are associated with genetic diseases, however more are not.

Antiserum Recognizing Irreversible Small Molecule (ISM) Chemical Compounds

High glucose Dulbecco's Modified Eagle Medium, fetal bovine serum, Medium 199, OPTI-MEM, 0.25% trypsin-EDTA 1× (Gibco, Grand Island, NY); Immobilon Western chemiluminescent HRP substrate, C18 Zip-tip (Millipore, Billerica, MA); phenyl vinyl sulfone, phenyl vinyl sulfonate, ethyl vinyl sulfone, BVT 948, NSC 95397, Bay 11-7082, Bay 11-9085, AMI-1 (Santa Cruz Biotechnology, Santa Cruz, CA); trypsin (Promega, Madison, WI); recombinant PRMT1, PRMT1 assay kit (BPS Bioscience, San Diego, CA); histone H4 (New England BioLabs, Ipswich, MA); recombinant glutathione reductase, glutathione reductase activity colorimetric assay Kit (BioVision, Milpitas, CA); antibodies: IMPDH1 (PAS-27792, Thermo Fisher Scientific Inc, Waltham, MA); Anti-dimethyl-Arginine Antibody, asymmetric (ASYM24) (07-414), Anti-dimethyl-Histone H4 (Arg3) Asymmetric Antibody (07-213-I), Anti-phosphotyrosine Antibody, 4G10® Platinum (05-1050) (Millipore, Billerica, MA); (Cell Signaling Technology, Danvers, MA); PRMT1 (B-2, sc-166963), PTP1B (D-4, sc-133259), glutathione reductase (C-10, sc-133245), vimentin (H-84, sc-5565) (Santa Cruz Biotechnology, Santa Cruz, CA); peroxidase-conjugated secondary antibodies, Dylight™ 488, fluorescein (FITC)-conjugated secondary antibodies (Jackson ImmunoResearch Laboratories, West Grove, PA) were purchased from manufacturers indicated in parentheses.

The antigen of PVS was prepared by coupling of the cysteine thiolate in reduced bovine serum albumin (BSA) to the terminal carbon of PVS under alkaline conditions. Two ml of BSA at 2 mg/ml in PBS was reduced by 50 mM 1,4-dithioerythreitol at 37° C. for 1 h. To this solution, 2 ml of 20% trichloroacetic acid was added. The mixture was mixed. Twenty ml ice-cold acetone was added and the mixture was mixed and kept at −20° C. overnight. The resulting precipitate following low-speed centrifugation was dissolved in 2 ml 0.1 M sodium carbonate buffer, pH 8.4, containing 4 mg PVS and the solution was incubated at 37° C. for 4 h. The protein samples were buffer-exchanged into PBS by centrifugal concentration using an Amicon device with a cutoff of 10 kDa (Millipore) and then used for routine subcutaneous immunizations in rabbits. Following eight biweekly injections, whole blood was collected from the anesthetized animals 10 days after the final injection.

Figure 1:
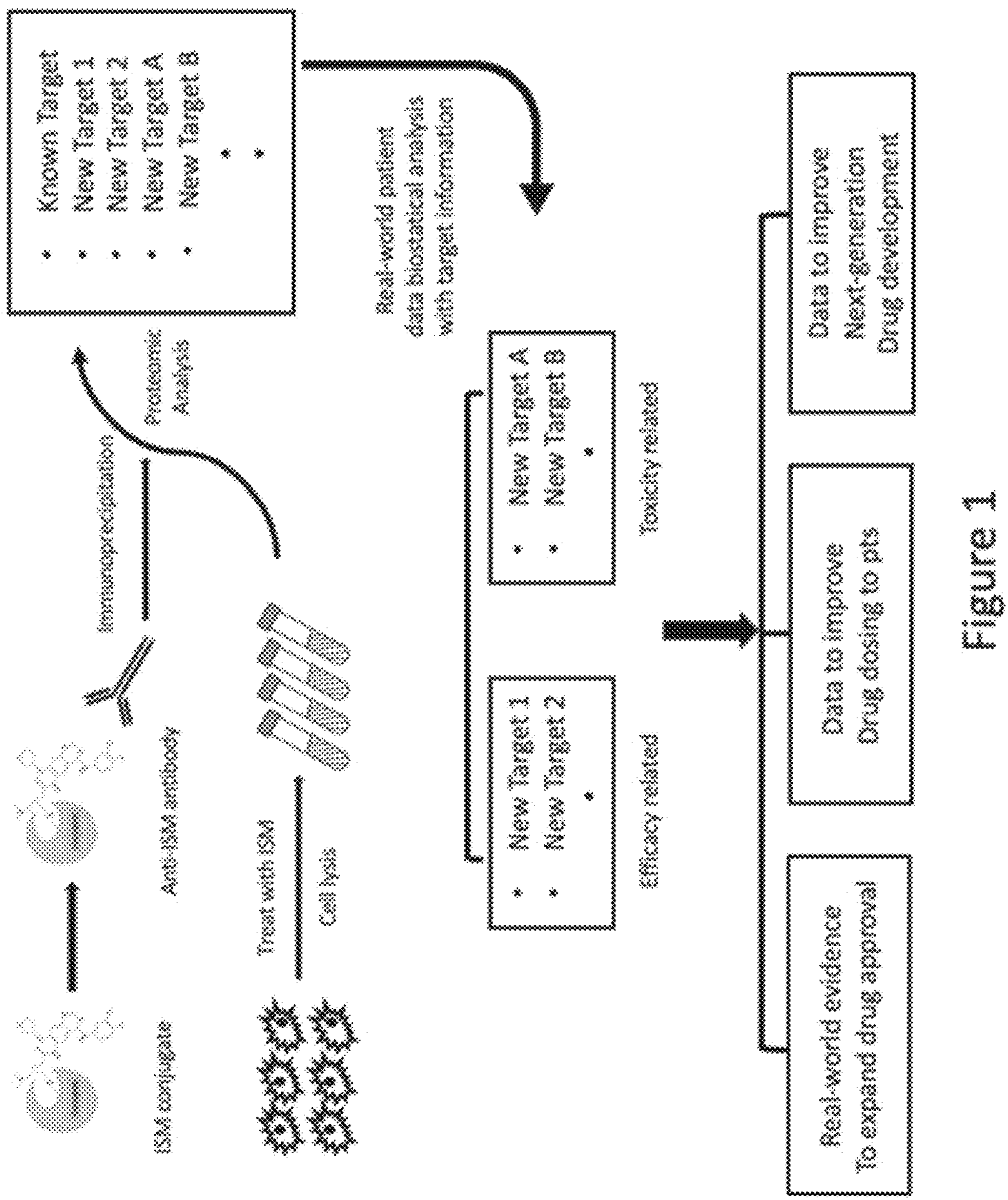
FIG. 1 shows systematic drawing and steps of the methods and systems of TISTA, or Target identification of Specific Tagging and Antibody Detection. Irreversible small molecule (ISM) chemical compound was conjugated to a protein carrier for raising antiserum against ISM. Immunoprecipitation and proteomic analysis was performed to obtain list of proteins bound to ISM. The list was compared to real-world clinical data and genes were separated into either efficacy related or toxicity related genes and real-world evidence was generated for either improvement of existing compounds to reduce toxicity and enhance efficacy or for expansion of clinical use, in accordance with various embodiments.
Figure 2:
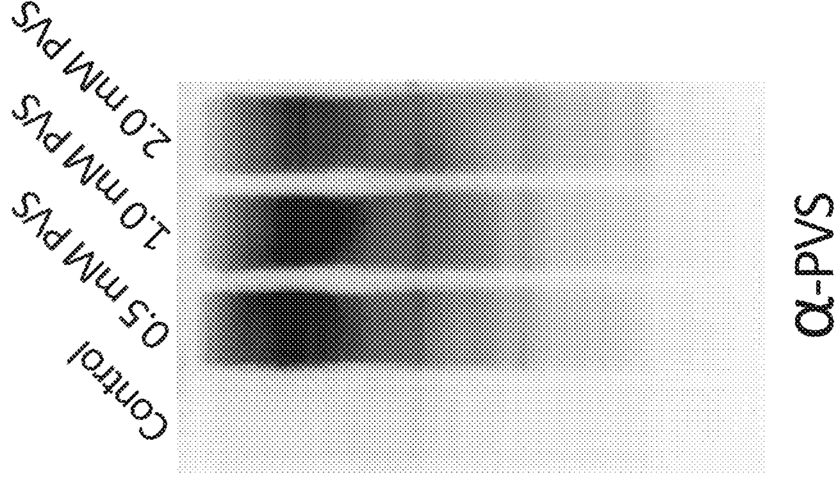
FIG. 2 describes example of phenyl vinyl sulfone (PVS) as a covalent protein tyrosine phosphatase (PTP) inhibitor. HeLa cells were treated with various concentrations of PVS in PBS for 1 h, washed with PBS for three times, and lysed with RIPA lysis buffer containing 10 mM 1,4-dithioerythritol. The proteins in the lysate were examined by Coomassie blue G-250 staining (left panel), and anti-PVS (right panel) following SDS-PAGE and electrotransfer. The control groups were treated with the same volume of DMSO. CBB: Coomassie blue G-250, α-pY: anti-phosphotyrosine, α-PVS: anti-PVS. The drawing is in accordance with various embodiments.
Figure 2:
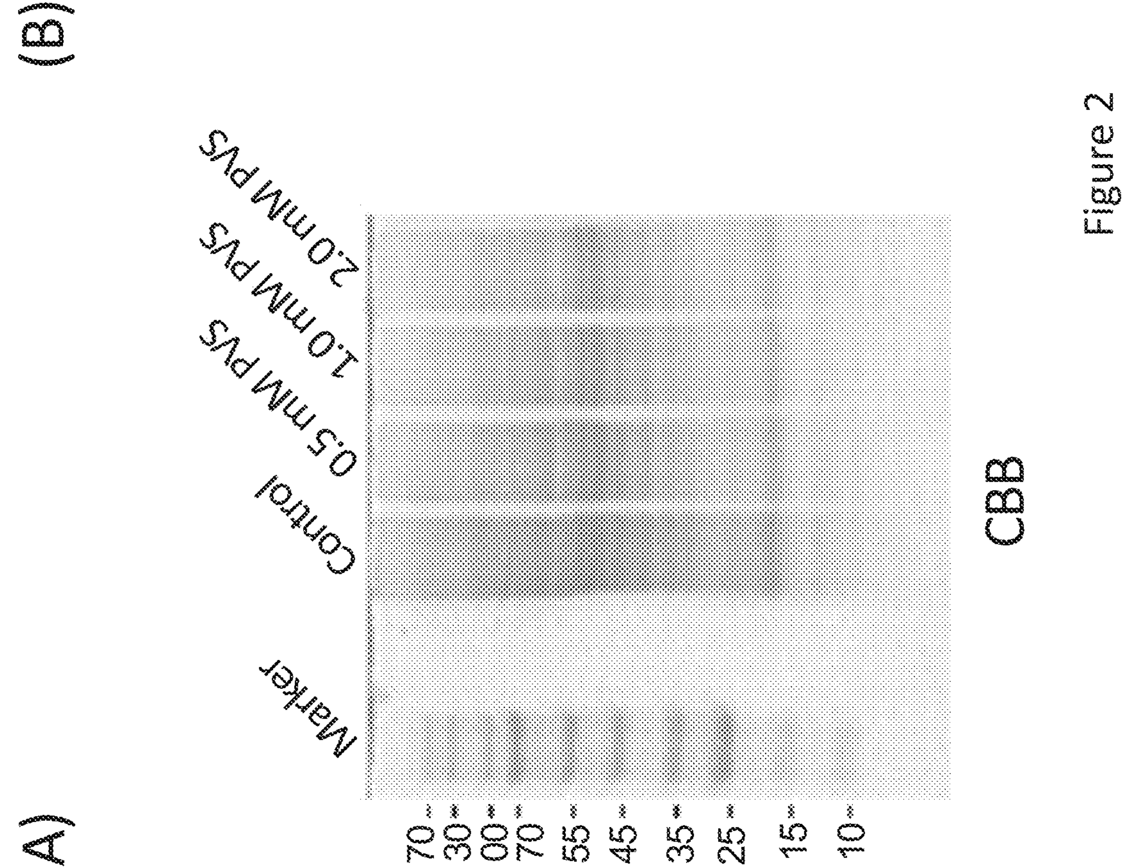

Based on the observations that PVS and PVSN were PTP covalent inhibitors (22), we attempted to develop an antiserum against PVS and use the antiserum in the identification of PVS-tagged proteins through immunoblotting and immunoprecipitation. First, we confirmed the inhibitory activity of PVS on PTPs and tested the efficacy of our antiserum against PVS. HeLa cells were treated with various concentrations of PVS for 1 h and the cell lysate was examined by SDS-PAGE and immunoblotting using the antisera against PVS (FIG. 2). Numerous proteins were covalently modified by PVS and revealed by the anti-PVS immunoblotting (FIG. 2). Higher concentrations of PVS elicited higher levels of PVS modification, but with the same pattern. The antiserum showed great specificity as evidenced by the lack of signal in the control group. Specificity of the anti-PVS was further tested by the combined treatment of ethyl vinyl sulfone (EVS) and PVS. HeLa cells were pretreated with 10 μM to 1 mM EVS in PBS for 30 min and then treated with 100 μM PVS in PBS for 1 h. Pretreatment of EVS at 100 μM and 1 mM significantly attenuated PVS modification suggesting that the antiserum recognition relies heavily on the phenyl functional group.

Figure 3:
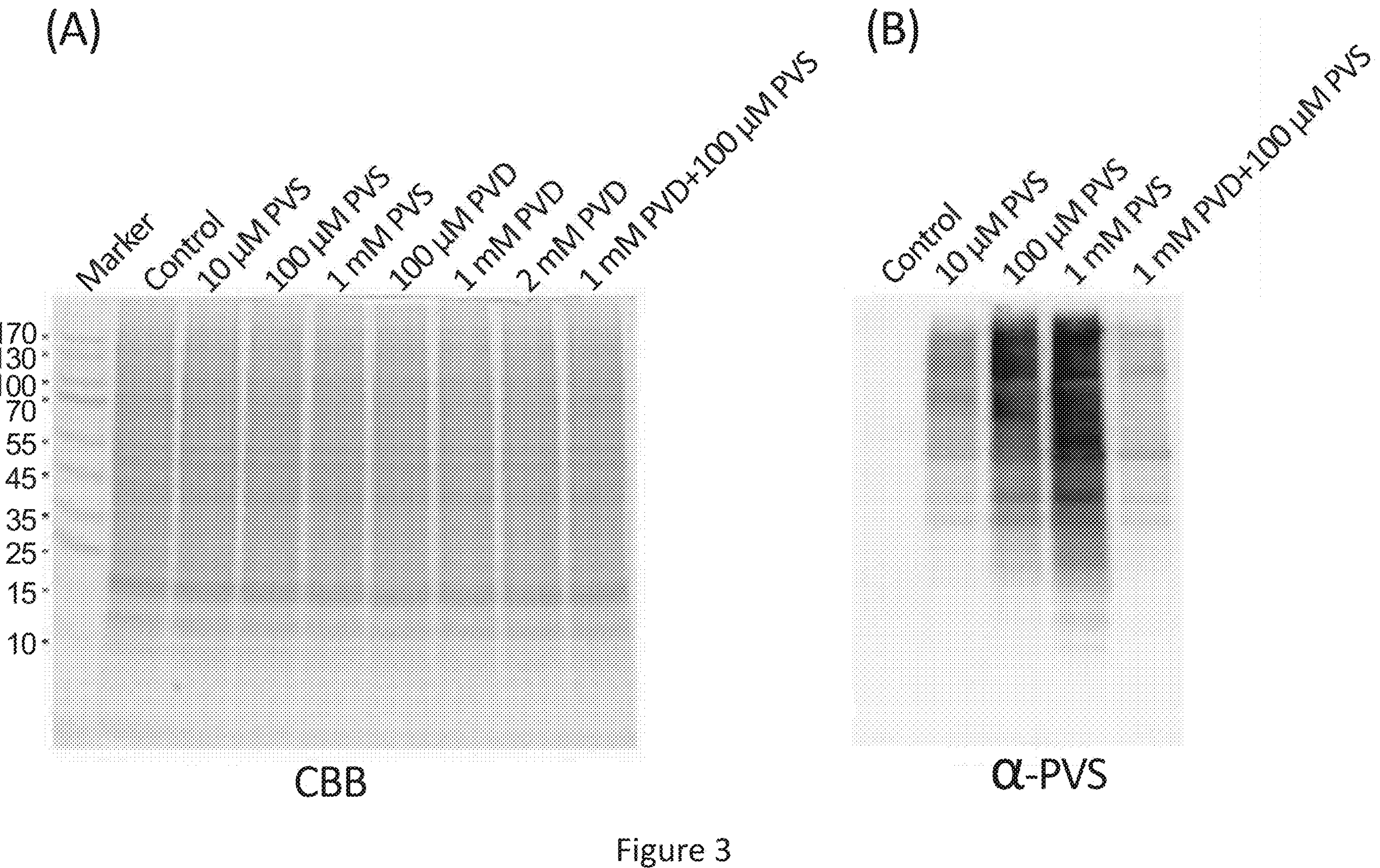
FIG. 3 shows example of competition of PVS labeling by a PTP inhibitor pervanadate (PVD) in HeLa cell. HeLa cells were treated with 10 μM to 1 mM PVS in PBS for 1 h or with 0.1-2 mM PVD in PBS for 30 min. In the case of PVS and PVD combined treatment, HeLa cells were pretreated with PVD for 30 min and then treated with PVS in PBS for 1 h. The cells were then lysed with RIPA lysis buffer containing 10 mM 1,4-dithioerythritol. The proteins in the lysate were examined by Coomassie blue G-250 staining (A), and anti-PVS (B) following SDS-PAGE and electrotransfer. The drawing is in accordance with various embodiments.

Pervanadate is an irreversible PTP inhibitor by oxidizing the active-site cysteine thiol of PTPs (24). If both PVS and pervanadate target the same thiol group, pretreatment of pervanadate would hinder the tagging of PVS. Indeed, pretreatment of HeLa cells with 1 mM pervanadate for 30 min completely blocked the tagging of PVS (FIG. 3). Similarly, treatment of HeLa cell lysate with 1 mM pervanadate and 100 μM PVS together almost completely blocked the tagging of PVS (FIG. 3). Next, we tested the competition of BVT 948 and NSC 95397 on the tagging of PVS. BVT 948 (25) and NSC 95397 (26) are PTP and dual specificity phosphatase inhibitors, respectively. Treatment of both drugs elicited increased amounts of tyrosine phosphorylation, albeit with different sensitivity and pattern. NSC 95397 blocked PVS tagging better than BVT 948 both in vitro and in cellulo. Therefore, the data indicate that PVS forms covalent bond with the cysteine thiol groups of cellular proteins, which can be blocked by the pretreatment of known PTP inhibitors.

Example was also described that anti-afatinib antiserum can be successfully raised and used to study novel afatinib interacting protein targets. The antigen was prepared by coupling of the cysteine thiolate in reduced ovalbumin (OVA) to the alpha carbon of acrylamide group in afatinib under alkaline conditions. This antiserum is able to detect protein targets covalently bound with afatinib. In addition, antiserum is capable of binding protein targets covalently bound with afatinib derivatives including, but not limited to, canertinib and dacomitinib, as described in example illustrated in FIGS. 8 and 10.

ISM Tagging In Vitro and in Cellulo

HeLa cells were obtained originally from American Type Culture Collection. Cells were cultured in Dulbecco's Modified Eagle Medium (DMEM), high glucose medium containing 10% fetal bovine serum (FBS) within 5% CO2 atmosphere at 37° C.

HeLa cells were cultured to about 90% confluence on a 10-cm dish in DMEM with 10% FBS ($5\times10^6$~$1\times10^7$ cells). HeLa cells were lysed by repeated pipetting with 900 μL 2% Triton X-100 in 20 mM Tris-HCl, pH 8.0. The lysate was centrifuged at 12,000×g for 10 min and the supernatant was aliquoted (200 μL) and treated with PVS, PVSN, or Bay 11-7082 of various concentrations at room temperature for 5 to 60 min. The stocks of 1000×PVS, 1000×PVSN, and 1000× Bay 11-7082 were prepared in DMSO. The reaction was stopped by adding 1,4-dithioerythreitol to a final concentration of 10 mM. The reaction solution was then mixed with equal volume of 2× SDS sample buffer. Ten μL sample solution was used for SDS gel electrophoresis and immunoblotting. The signal of GAPDH was used to adjust the amount of protein loading.

HeLa cells were cultured to about 90% confluence on 10-cm dish in DMEM with 10% FBS (5×106~1×107 cells) for experiments. For PVS treatment, HeLa cells were refreshed with DMEM containing 10% FBS and various concentrations of PVS in the presence or absence of protein tyrosine phosphatase inhibitor such as pervanadate, BVT 948, or NSC 95397 for 5 to 60 min. For PVSN or Bay 11-7082 treatment, HeLa cells were washed with phosphate-buffered saline (PBS) and treated with PVSN or Bay 11-7082 in PBS for 5 to 60 min. The stock of 500× pervanadate was prepared in water. The stocks of 50 mM BVT 948, and 50 mM NSC 95397, 1000× PVS, 1000× PVSN, and 1000× Bay 11-7082 were prepared in DMSO solution. Each group contained the same volume of DMSO. After treatment, the cells were washed with PBS twice and lysed with 900 μL Radio-Immunoprecipitation Assay (RIPA) lysis buffer containing 10 mM 1,4-dithioerythritol. The solution was then mixed with equal volume of 2× SDS sample buffer. Ten μL sample solution was used for electrophoresis and immunoblotting. The signal of anti-GAPDH was used to adjust the amount of protein loading.

Figure 4:
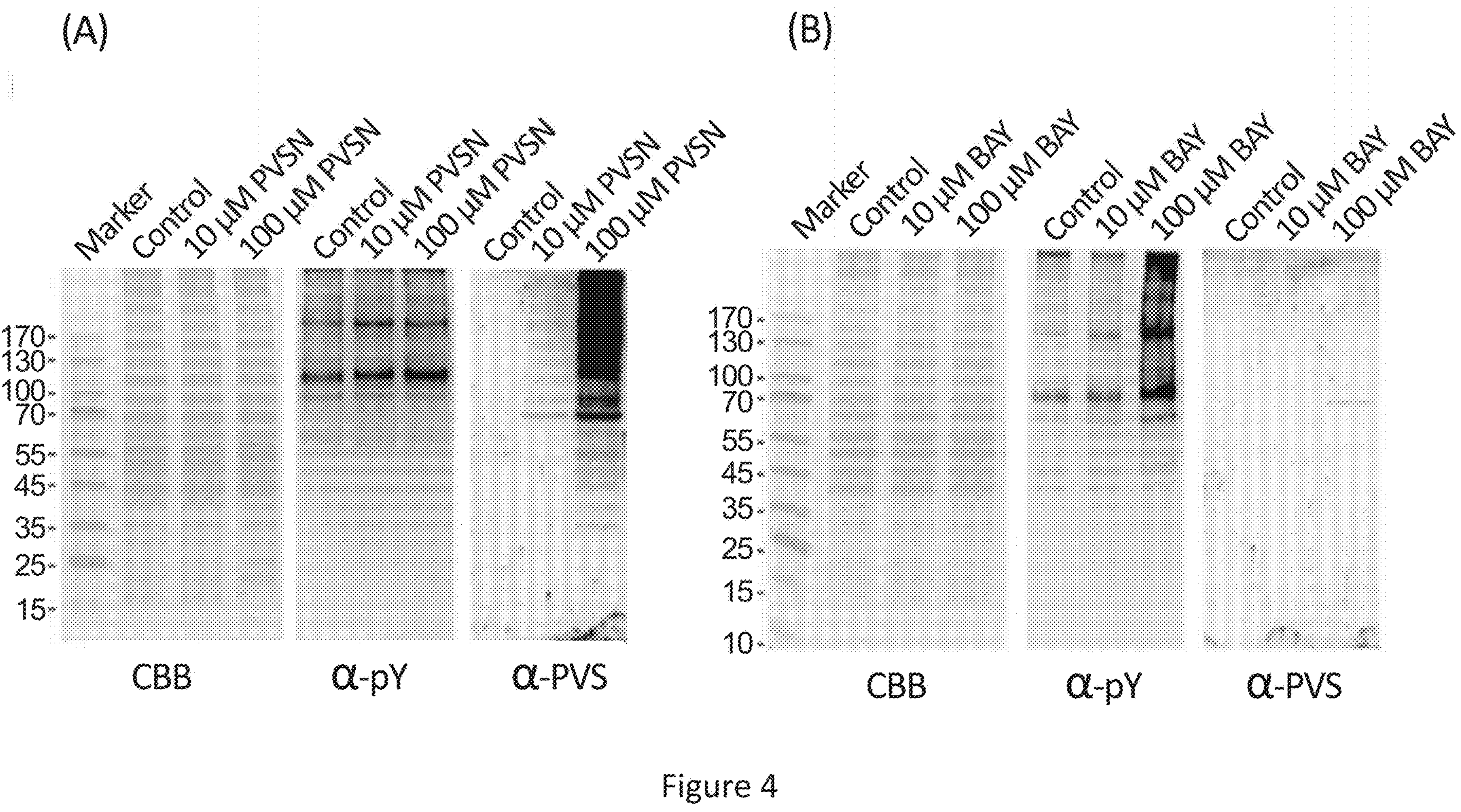
FIG. 4 describes use of anti-PVS in recognition of PVSN and Bay 11-7082 adducts. HeLa cells were treated with various concentrations of PVSN (A) or Bay 11-7082 (B) in PBS for 5 min, washed with PBS for three times, and lysed with RIPA lysis buffer containing 10 mM 1,4-dithioerythritol. The proteins in the lysate were examined by Coomassie blue G-250 staining, immunoblotting with anti-phosphotyrosine and anti-PVS following SDS-PAGE and electrotransfer. The control groups were treated with the same volume of DMSO. CBB: Coomassie blue G-250, α-pY: anti-phosphotyrosine, α-PVS: anti-PVS. The drawing is in accordance with various embodiments.

We next examined whether anti-PVS antiserum can be used in detection of target proteins probed by PVS analogs such as PVSN and Bay 11-7082. Treatment of PVSN and Bay 11-7082 at concentrations of 10 and 100 μM for 5 min increased the levels of phosphotyrosine modification in HeLa cells, especially Bay 11-7082 at 100 μM (FIG. 4) confirming their effects in PTP inhibition. PVSN-tagged proteins were abundantly recognized by anti-PVS antiserum (FIG. 5A), but only few Bay 11-7082-tagged proteins were detected by the anti-PVS antiserum (FIG. 5B). Therefore, anti-PVS antiserum can be readily used in the detection of proteins modified by PVS and PVSN.

For the effects of PVS, PVSN, Bay 11-7082, Bay 11-7085, or AMI-1 on protein arginine methylation, HeLa cells were cultured to about 90% confluence on 10-cm dish in DMEM with 10% FBS ($5\times10^6$~$1\times10^7$ cells). After washing the HeLa cells with 10 mL DMEM once, the cells were cultured for additional 1 or 3 h in 10 mL DMEM containing PVS, PVSN, Bay 11-7082, Bay 11-7085, or AMI-1. The stocks of 1000× PVS, 1000× PVSN, 1000× Bay 11-7082, and 1000× Bay 11-7085 were prepared in DMSO solution, but 500× AMI-1 in ethanol. Each group contained the same volume of DMSO and ethanol. After wash with TBS for three times, the cells were lysed with 900 μL RIPA lysis buffer and centrifuged to pellet down the debris. The supernatant was then transferred to a new tube and mixed with equal volume of 2×SDS sample buffer. Ten μL sample solution was for electrophoresis and immunoblotting. The signal of anti-GAPDH was used to adjust the amount of protein loading.

In order to find out the identity of PVS- or PVSN-tagged proteins, we used anti-PVS antiserum to pull down potential targets of PVS or PVSN in HeLa cells treated with 1 mM PVS or PVSN for 30 min. Cell lysates of control, PVS- or PVSN-treated HeLa cells were processed with immunoprecipitation by anti-PVS to obtain proteins potentially tagged by PVS or PVSN. In addition, tryptic peptides were prepared and used for immunoprecipitation by anti-PVS antiserum to reveal the modification sites. The false discovery rates were set to 0.01 for peptides, proteins and sites by target-decoy strategy to distinguish correct and incorrect identifications, with a cut-off adjusted p value≤0.05. We assumed positive protein identification results when the Mascot scores of PVS- and PVSN-tagged proteins was higher than 50 and at least two-fold higher than the corresponding control. The resulting data were summarized, and 183 candidates are listed in Supplementary Table S1. There are 103 target proteins tagged both by PVS and PVSN, 70 by PVS only and 10 by PVSN only. It appears that PVS is less selective than PVSN in covalently tagging the target proteins. Surprisingly, only one PTP was found, the low molecular weight PTP, in the PVS-tagged proteins. One major concern of proteomics is that Mass spectrometer has a limited capacity in detecting low-abundance proteins (peptides) in samples with a wide range of relative abundance. Therefore, specific enrichment protocols are required for uncovering those low-abundance targets (27). The data indicate that PVS and PVSN are not only reactive towards PTPs, but also other proteins, especially those with highly reactive cysteine residues or prone to oxidation (28, 29). It is generally believed that proteins with low pKa thiols are susceptible to oxidation since thiolates are much stronger nucleophiles than thiol groups (30, 31), and we marked proteins containing reactive cysteine or cysteine prone to oxidation with * or # respectively as shown in Supplementary Table S1 (28, 29). Modification sites of some PVS and PVSN targets were also determined with high confidence (Supplementary Table S2 and S3). However, attempts to pull down Bay 11-7082-tagged proteins by anti-PVS were not successful.

Figure 5:
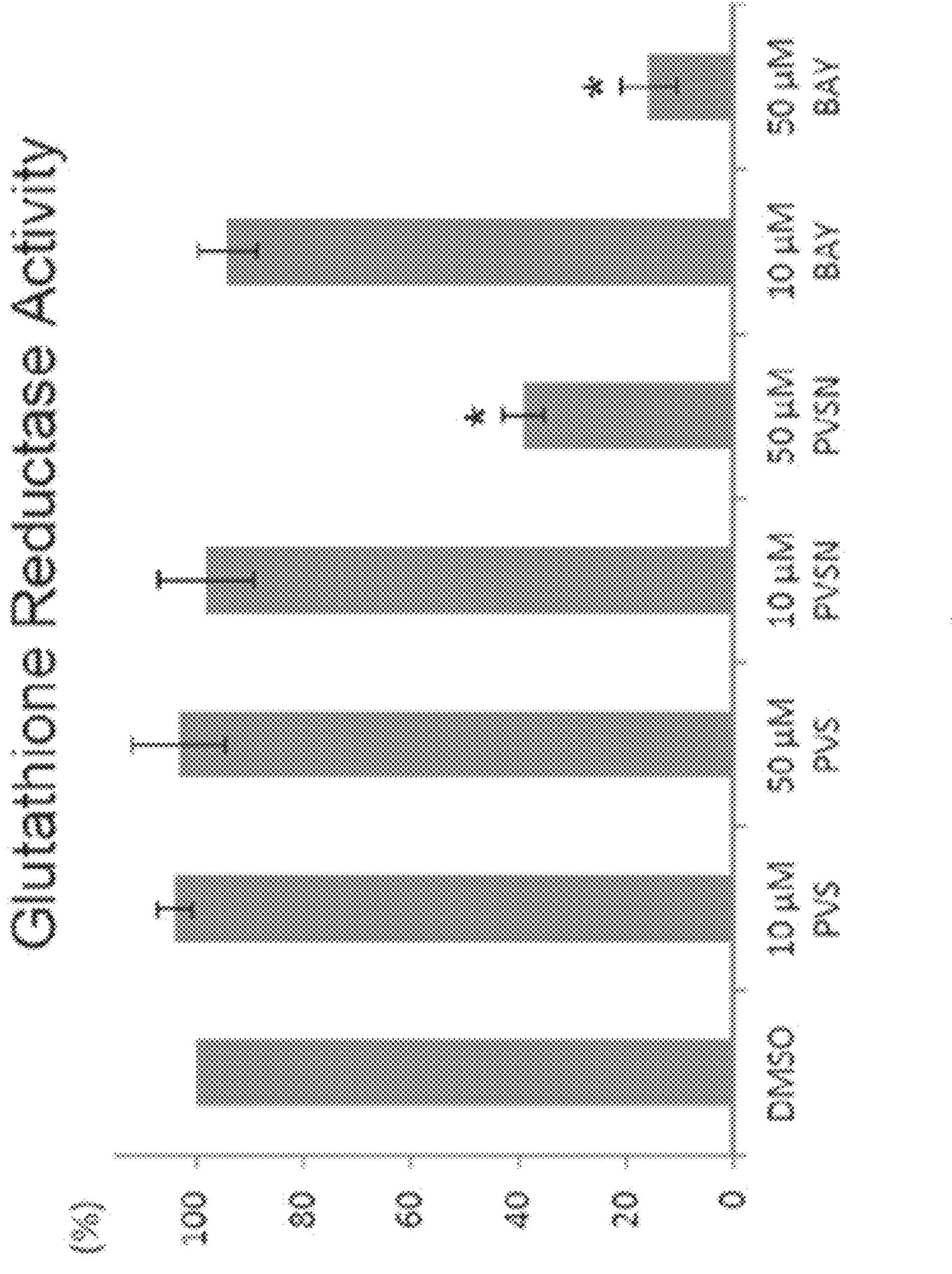
FIG. 5 shows effects of PVS, PVSN, and Bay 11-7082 on the in vitro enzyme activity of glutathione reductase. Recombinant glutathione reductase was first treated with NADPH and 10 or 50 μM PVS, PVSN or Bay 11-7082 for 1 h at room temperature. In the control group, recombinant glutathione reductase was treated with NADPH and the same volume of DMSO used in the treatment of drugs in the assay buffer. Following the addition of oxidized glutathione, the decrease in absorbance at A340 was monitored over 10 min. Results were presented as mean of three independent experiments plus and minus standard deviation. (Compared to DMSO, *: $p<0.001$.) The drawing is in accordance with various embodiments.
Figure 6:
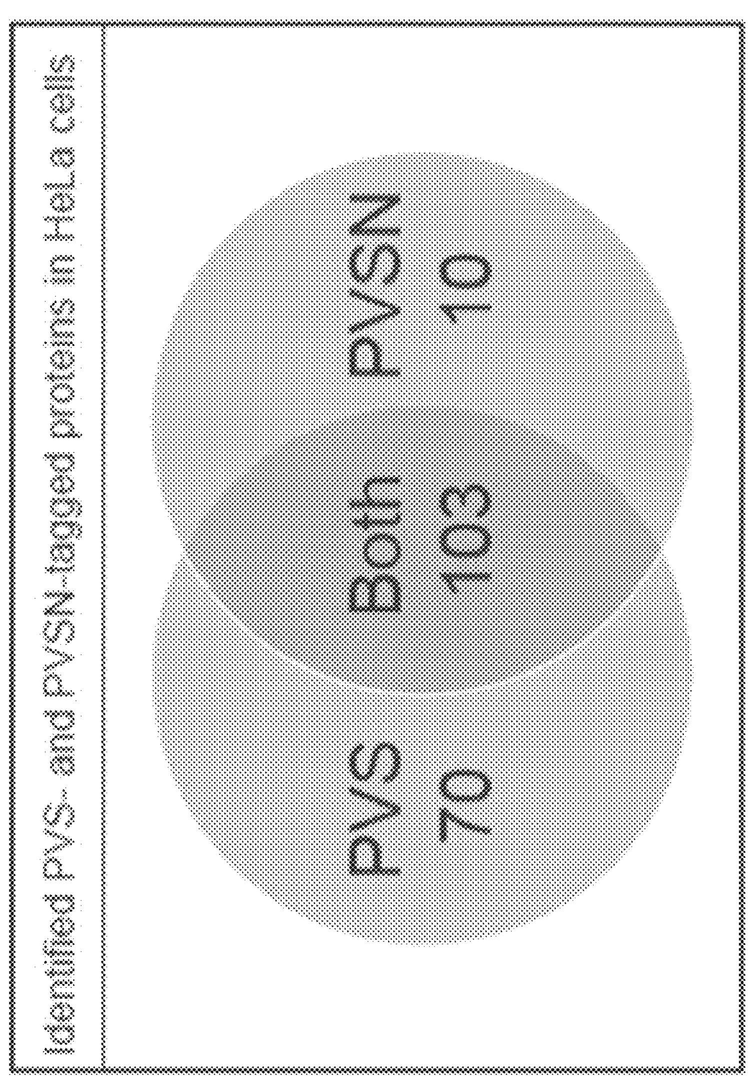
FIG. 6 is a diagram of analysis results showing relation and hit numbers between targets found with PVS and PVSN. The drawing is in accordance with various embodiments.
Figure 7:
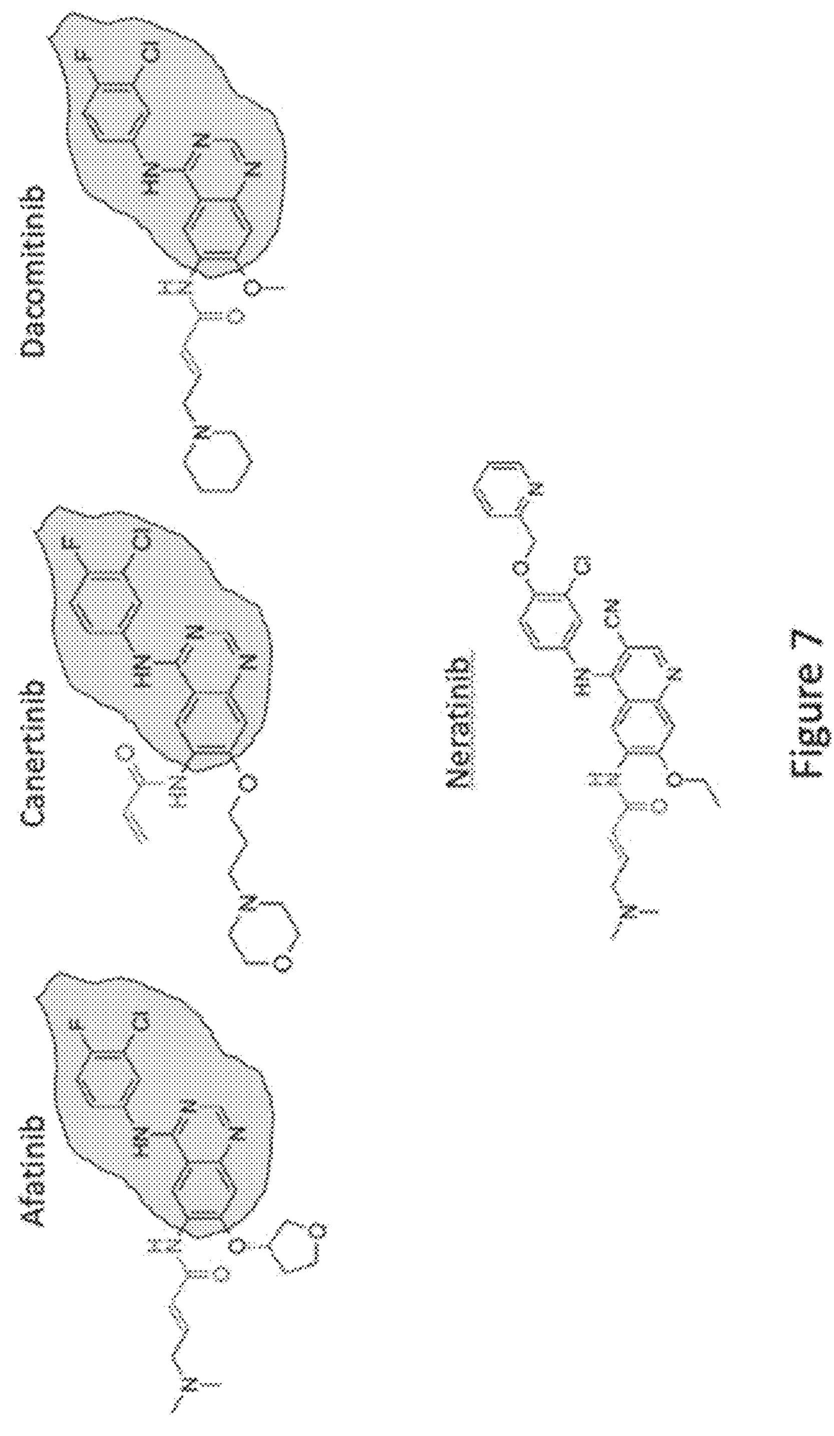
FIG. 7 indicates drawing of chemical structure of afatinib and its derivatives, canertinib, dacomitinib, and neratinib. Common structure portion of afatinib, canertinib, and dacomitinb, recognized by antiserum, are covered by shaded area. This common structure is absent in neratinib, which is not recognized by the antiserum.

We then chose protein arginine methyltransferase 1 (PRMT1), glutathione reductase, vimentin and inosine-5'-monophosphate dehydrogenase 1 (IMPDH1) for further study due to our interest and their relatively high scores in the proteomics data. Immunoprecipitation was carried out with anti-PVS in cell lysate prepared from HeLa cells treated with PVS or PVSN and the immunoprecipitate was subjected to immunoblotting (FIG. 5). For IMPDH1, cell lysate was immunoprecipitated with anti-IMPDH1 followed by immunoblotting with anti-PVS. The results confirmed that PRMT1, glutathione reductase and IMPDH1 were indeed tagged by PVS or PVSN in cells treated with PVS or PVSN. Whether vimentin was tagged by PVS or PVSN was inconclusive since its signal was also present in the control group. However, modification site was identified by Mass spectrometric analysis suggesting that vimentin is indeed tagged by PVS or PVSN. Therefore, the data indicate that both PVS and PVSN are not specific for PTPs. They form covalent adducts with a wide variety of proteins other than PTPs.

Figure 9:
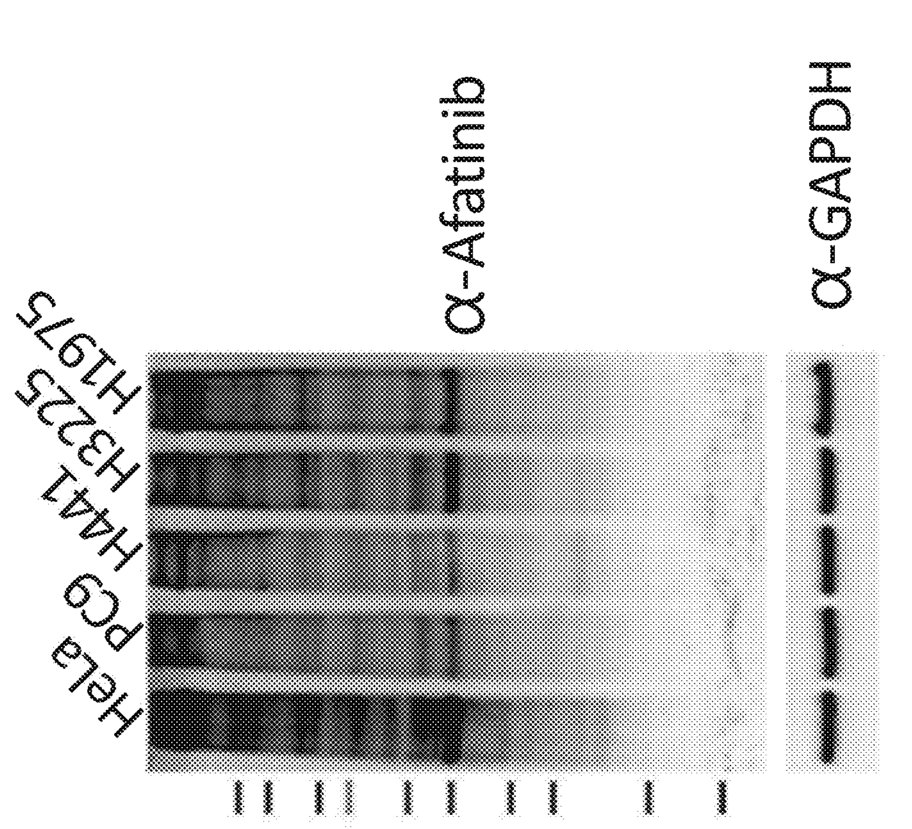
FIG. 9 panel (A) describes example of afatinib as a TKI in various cell lines, HeLa, PC9, H441, H3225, and H1975.
Figure 9:
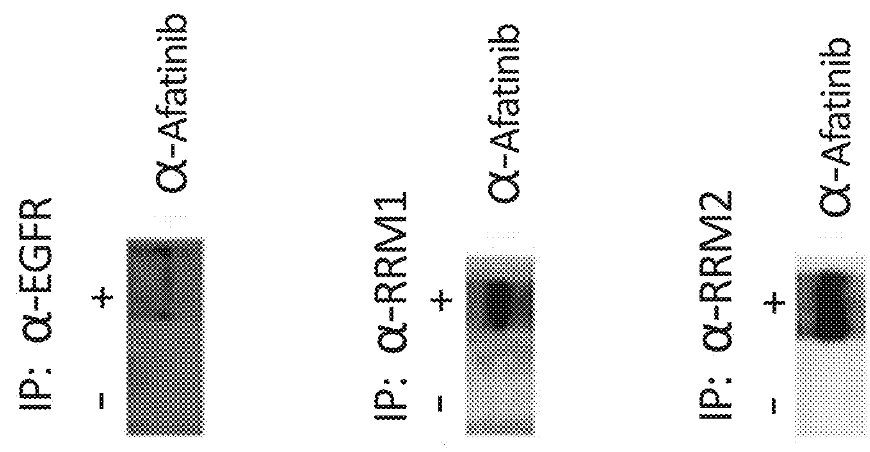

Example was shown to illustrate studies using anti-afatinib antiserum for examination of cellular lysate. We treated PC-9 cells in culture with the various concentrations of afatinib for 1 h and the cell lysate was examined by SDS-PAGE and immunoblotting with the anti-afatinib antiserum. Unexpectedly, numerous proteins were covalently modified by afatinib as showed by the anti-afatinib immunoblotting. However, this antiserum showed high specificity as evidenced by the lack of signal in the control group treated with solvent only and groups treated with low concentrations of afatinib. The signals were readily observed when cells were treated with 1 μM afatinib, and 10 μM afatinib gave rise to higher intensity of signals. Thus, we chose the concentration of 10 μM afatinib in the time-dependent experiments. With increasing incubation time, the intensity of signal increased with an almost identical pattern. In addition, we also performed the afatinib labeling at three pH values. HeLa cells were treated with 10 μM afatinib at pH 6.2, 7.2, and 8.2 for 1 h in culture. The signal of pH 6.2 was weak, and the patterns between pH 7.2 and pH 8.2 were very similar. All tested pH values are lower than the typical pKa of the side chain of cysteine residues. Reactions at a lower pH value appeared to attenuate the afatinib labeling due to the decrease in thiolate formation at the cysteine residues in proteins, confirming the Michael addition mechanism underlying afatinib labeling. Interestingly, the anti-afatinib antiserum can be used to monitor the labeling of other covalent drugs sharing similar structures; canertinib and dacomitinib (FIG. 10). However, the signal of neratinib was undetectable probably due to the lack of the N-chloro-fluorophenyl moiety which is present in afatinib, canertinib, and dacomitinib. The higher intensity of canertinib labeling may result from the greater reactivity of canertinib, but not from better recognition by the antiserum. On the other hand, we chose other lung cancer cell lines, H441 (wild-type EGFR), H3225 (L858R EGFR), H1975 (L858R, T790M EGFR), to test whether the mutations in EGFR could influence the afatinib labeling. The results (FIG. 9A) showed that there were only slight differences in the afatinib-labeling protein patterns among these four lung cancer cell lines. As EGFR is the known target of afatinib, we attempted to confirm this notion by immunoprecipitation with anti-EGFR antibody followed by immunoblotting with anti-afatinib antiserum using detergent extract from HeLa cells treated with or without 10 μM afatinib for 1 h in culture. As shown in FIG. 9B, the data indicate that EGFR can be labeled by afatinib in living cells treated with this drug.

Immunoprecipitation and Proteomic Analysis

After treatment with 10 μM afatinib for 1 h, the treated PC-9 cells were lysed with a lysis buffer (50 mM MOPS, pH 7.20, 100 mM NaCl, 1 mM EDTA, 5% glycerol, and 1% NP-40) containing protease inhibitor cocktails. After centrifugation, the supernatant was added with SDS to a final concentration 0.3% and heated at 65° C. for 10 min. The solution was cooled on ice and added with 9× volume of the lysis buffer to dilute the SDS. Then, the solution was added with anti-afatinib and incubated at 4° C. overnight. The antibody was then pulled down by protein A-conjugated resin and washed by the lysis buffer for three times. Proteins were eluted by SDS sample buffer. For immunoprecipitation of EGFR, RRM1, and RRM2, the supernatant was directly added with primary antibody and incubated at 4° C. overnight. The antibody was then pulled down by protein A-sepharose and washed by the lysis buffer three times. Proteins were then eluted by SDS sample buffer.

After the SDS-PAGE fractionation, the gel band was cut into small pieces and reduced with 1,4-dithioerythreitol (50 mM) at 37° C. for 1 h and alkylated with iodoacetamide (100 mM) at room temperature for 1 h. The gel pieces were destained repeatedly with 25 mM ammonium bicarbonate in 50% acetonitrile until became colorless. Gel slices were dehydrated with 100% acetonitrile for 5 min and vacuum-dried for 5 min. The followed enzymatic hydrolysis was carried out with trypsin at an enzyme-to-substrate ratio of 1/40 at 37° C. for 16 h. The tryptic peptides were extracted twice with 50% acetonitrile containing 5% formic acid under moderate sonication for 10 min and dried completely under vacuum. The peptide mixtures were desalted by C18 Zip-tip and subjected to downstream MS analysis.

The samples were reconstituted in 9% acetonitrile and 0.1% formic acid to give a volume of 4 μL, and loaded onto a C18 column of 75-μm×250-mm (nanoACQUITY UPLC BEH130, Waters). The peptides mixtures were separated by online nanoflow liquid chromatography using nanoAcquity system (Waters) with a linear gradient of 5 to 50% acetonitrile (in 0.1% formic acid) in 95 min, followed by a sharp increase to 85% acetonitrile in 1 min and held for another 15 min at a constant flow rate of 300 nl min-1. Peptides were detected in an LTQ-OrbitrapVelos hybrid mass spectrometer (Thermo Scientific) using a data-dependent CID Top20 method in positive ionization mode. For each cycle, full-scan MS spectra (m/z 300-2000) were acquired in the Orbitrap at 60,000 resolution (at m/z 400) after accumulation to a target intensity value of 5×106 ions in the linear ion trap. The 20 most intense ions with charge states≥2 were sequentially isolated to a target value of 10,000 ions within a maximum injection time of 100 ms and fragmented in the high-pressure linear ion trap by low-energy CID with normalized collision energy of 35%. The resulting fragment ions were scanned out in the low-pressure ion trap at the normal scan rate and recorded with the secondary electron multipliers. Ion selection threshold was 500 counts for MS/MS, and the selected ions were excluded from further analysis for 30 s. An activation q=0.25 and activation time of 10 ms were used. Standard mass spectrometric conditions for all experiments were: spray voltage, 1.8 kV; no sheath and auxiliary gas flow; heated capillary temperature, 200° C.; predictive automatic gain control (AGC) enabled, and an S-lens RF level of 69%. All MS and MS/MS raw data were processed with Proteome Discoverer version 1.3 (Thermo Scientific), and the peptides were identified from the MS/MS data searched against the Swiss-Prot (540732 sequences entries) database using the Mascot search engine 2.3.02 (Matrix Science). Search criteria used were as follows: trypsin digestion; considered variable modifications of cysteine PVS-modification (+168.0245 Da), PVSN-modification (+184.01942 Da), glutamine deamidation (+0.98402 Da), methionine oxidation (+15.9949 Da), and cysteine carboxyamidomethylation (+57.0214 Da); up to three missed cleavages were allowed; and mass accuracy of 10 ppm for the parent ion and 0.6 Da for the fragment ions. The significant peptide hits defined as peptide score must be higher than Mascot significance threshold ($p<0.05$) and therefore considered highly reliable, and that manual interpretation confirmed agreement between spectra and peptide sequence. After data acquisition, the individual MS/MS spectra within a single LC run were combined, smoothed, deisotoped using the MicromassProteinLynx™ Global Server (PGS) 2.2 and output as a single peak list (.pkl) file. The peak list files were used to query the Swiss-Prot database (SwissProt 54.1; 277883 sequences; 101975253 residues) using the MASCOT program (Version: 1.9.05) with the following parameters: peptide mass tolerance, 50 ppm; MS/MS ion mass tolerance, 0.25 Da; enzyme digestion was set to trypsin allow up to one missed cleavage; variable modifications considered were methionine oxidation and cysteine carboxyamidomethylation.

In 1 mL solution containing 100 μM cysteine, 100 μM PVS, PVSN or Bay 11-7082 in 20 mM $NaHCO_3$, pH 8.4, reaction was held at 37° C. for 60 min. The resulting reaction products were subjected directly to the LC-ESI-MS analyses. The LC-ESI-MS system consisted of an ultra-performance liquid chromatography system (Ultimate 3000 RSLC, Dionex) and an electrospray ionization (ESI) source of quadrupole time-of-flight (TOF) mass spectrometer (maXis HUR-QToF system, BrukerDaltonics). The samples were kept in an autosampler at 4° C. Separation was performed with reversed-phase liquid chromatography (RPLC) on a BEH C18 column (2.1×100 mm, Walters). The elution started from 99% mobile phase A (0.1% formic acid in ultrapure water) and 1% mobile phase B (0.1% formic acid in ACN), held at 1% B for 0.5 min, raised to 60% B in 6 min, further raised to 90% B in 0.5 min, held at 90% B for 1.5 min, and then lowered to 1% B in 0.5 min. The column was equilibrated by pumping 1% B for 4 min. The flow rate was set 0.4 ml/min with injection volume 2 μl. LC-ESI-MS chromatogram were acquired under following conditions: capillary voltage of 4,500 V in positive ion mode, dry temperature at 190° C. dry gas flow maintained at 81/min, nebulizer gas at 1.4 bar, and acquisition range of m/z 100-1000.

Functional Analysis of Enzymatic Activity

The assay was carried out according to the protocol provided by BioVision Inc. (Catalog number K761-200). Recombinant glutathione reductase was first treated with NADPH and 10 μM or 50 μM PVS, PVSN or Bay11-7082 for 30 min at room temperature. In the control group, recombinant glutathione reductase was treated with NADPH and the same volume of DMSO used in the treatment of drugs in the assay buffer. Following the addition of oxidized glutathione, the decrease in absorbance at A340 was monitored over 10 min.

The reaction mixture contained 100 ng recombinant PRMT1, 1 μg full-length recombinant Histone H4, 1 μM S-adenosylmethionine, various concentrations of PVS, PVSN, Bay 11-7082 or AMI-1 in a total volume of 100 μl in PBS, pH 7.4. The reaction was incubated at 37° C. for 30 min and 10 μl of the reaction product was examined by SDS-PAGE and immunoblotting with anti-PVS and anti-H4R3me2a.

Based on the proteomic results, we first examined whether PVS, PVSN and Bay 11-7082 affected the activity of glutathione reductase (FIG. 5). All compounds were ineffective in inhibiting glutathione reductase at 10 μM. However, PVSN and Bay 11-7082 at 50 μM inhibited the activity of glutathione reductase by 61% and 74%, respectively. It is highly possible that PVSN and Bay 11-7082 inhibit glutathione reductase at high concentrations by tagging one of the cysteine residues (Cys58) involved in the catalytic reduction of oxidized glutathione (32) (Supplementary Table S3). A previous report also supports this result by showing that Bay 11-7082 inhibited GR activity in erythrocytes (33).

Protein arginine methylation catalyzed by PRMTs results in the addition of methyl groups to the nitrogen atoms of the arginine side chains in the forms of monomethylated (NG-monomethylarginine), symmetrically dimethylated (NG, N'G-dimethylarginine) and asymmetrically dimethylated arginine (NG,NG-dimethylarginine; ADMA). Multiple cellular processes, including chromatin structure, signal transduction, transcriptional regulation, RNA metabolism, and DNA damage repair are regulated by protein arginine methylation (34). PRMT1 is responsible for most ADMA formation in cells (35) such as histone H4 arginine 3 (H4R3) ADMA (36, 37). The protein identification and modification site identification results suggest PVS or PVSN may serve as an inhibitor of PRMT1. Especially, one highly reactive cysteine residue was tagged by iodoacetamide (28) and PVS (Supplementary Table S2), whose tagging may lead to inactivation of PRMT1 (28). In vitro PRMT1 activity assay using recombinant PRMT1, histone H4, and S-adenosylmethionine in the presence of PVS, PVSN or Bay 11-7082 was conducted. Bay 11-7082 at 2.5 μM, PVSN at 5 μM and PVS at 10 μM caused significant inhibition of methylation of histone H4. AMI-1, a well-known inhibitor of PRMT1 (38), was used for comparison. The results indicate that PVSN and Bay 11-7082 are close to AMI-1 in PRMT1 inhibitor potency using histone H4 as a substrate. Based on the results in FIG. 8A, we calculated the IC50 of PVS, PVSN, Bay 11-7082, and AMI-1 as 23.32 μM, 10.38 μM, 10.72 μM, and 10.4 μM respectively by direct curve-fitting logistic regression analysis using the data of 5 μM, 10 μM, and 100 μM treatments. Three-point IC50 curves may provide an estimation, but certainly not an accurate calculation (data is not shown). Interestingly, adduct of Bay 11-7082 with PRMT1 can be recognized by anti-PVS. Our previous data showed that only few Bay 11-7082-tagged proteins were detected by the anti-PVS antiserum. We then examined the reactivity of PVS, PVSN and Bay 11-7082 with free cysteine in mild alkaline solution and examined the reaction products with LC-ESI-MS analysis (FIG. 5). PVS and PVSN readily formed adducts with cysteine through the expected Michael addition reaction, and we noticed an additional trace products appearing in the PVSN-cysteine reaction. However, the major reaction product of Bay 11-7082 with cysteine was obtained through substitution at the C3 position, but not by Michael addition. The data indicate that PVS, PVSN and Bay 11-7082 are all inhibitors of PRMT1 in vitro through covalent modification of the enzyme and these compounds can serve as the lead compound of PRMT1 inhibitor development.

Bay 11-7082 as a PRMT1 Inhibitor in Cellulo

Since Bay 11-7082 inhibited PRMT1 activity in an in vitro assay, we then tested the inhibitory activity of this compound in cultured HeLa cells. The levels of ADMA are regulated by both methylation and demethylation. Protein arginine dimethylation levels do not seem as dynamic as protein tyrosine phosphorylation levels since ADMA levels decreased only by 50% seven days after induction of PRMT1 knockout in mouse embryonic fibroblast (39). Some proteins of ADMA persisted several days in the absence of PRMT1. Interestingly, treatment of Bay 11-7082 in the cell culture condition for 3 h led to decline of levels in asymmetric dimethylarginine (ADMA) of 25 and 35 kDa (left panel, Supplementary FIG. 5). We also used histone H4R3 asymmetric dimethylation antibody as one kind of pan ADMA antibody (right panel, Supplementary FIG. 5). However, we noticed that the ADMA signals of one or two proteins increased in this experiment possibly due to the compensation activity caused by other PRMT family proteins (39) or disturbance of cell cycle progression affected by other target proteins of Bay 11-7082 (40). It is of interest to note that phenylsulfonyl structure present in Bay 11-7082 is also found in a PRMT1 inhibitor, C-7280948 (41), indicating the Bay 11-7082 could be a good lead compound for developing PRMT1 inhibitors. Therefore, we further compared the effects of PVS, PVSN, Bay 11-7082, Bay 11-7085 and AMI-1 under the cell culture conditions. We included another Bay 11-7082 analog, Bay 11-7085 for comparison (42, 43). Surprisingly, PVS at 50 μM did not change the levels of protein ADMA in cell culture, but PVSN at 50 μM decreased the levels of protein ADMA slightly. Treatments of Bay 11-7082 or Bay 11-7085 at concentration higher than 25 μM for 1 h led to decline of signals of ADMA. By the short-term treatment, AMI-1 at 50 μM had little effect on the general protein ADMA although 7-day treatment of AMI-1 in HeLa cells led to decrease in arginine methylation of Npl3 protein (38). The data indicate that PVSN, Bay 11-7082 and Bay 11-7085 are effective in cellulo in decreasing the levels of protein ADMA possible due to the inhibition of PRMT1.

Since many unexpected proteins were ably labeled by afatinib in lung cancer cells, we set up to identify potential targets of afatinib in PC-9 cells using immunoprecipitation and LC/MS-MS analysis. For the positive protein identification, q-values were set to 0.01 for both peptides and proteins by controlling the target-decoy strategy to distinguish correct and incorrect identifications. Surprisingly, several deoxyribonucleotide biosynthetic enzymes were found to be potential target proteins of afatinib. RNR received our attention due to its importance as a therapeutic target for cancer drug development. We then used anti-RRM1 antibody or anti-RRM2 antibody to pull down RRM1 or RRM2 from PC-9 cells after afatinib treatment. Indeed, immunoblotting with anti-afatinib antiserum confirmed the tagging of RRM1 or RRM2 with afatinib (FIG. 9B). The results showed that RNR was a target protein of afatinib and both subunits formed covalent adducts with afatinib. Thus, the anti-afatinib antiserum is useful for immunoblotting and immunoprecipitation.

To determine the modification sites tagged by afatinib on RNR, we incubated recombinant RRM1 or RRM2 protein with afatinib. The reaction product was examined by immunoblotting using anti-afatinib antiserum. As shown in FIG. 2A, the results showed that RRM1 protein was apparently modified by afatinib, and RRM2 protein was slightly modified by afatinib. However, RRM2 was modified by afatinib to a more extent when RRM1 and RRM2 were mixed at one to one ratio. After photography, the gel band was excised and processed to determine the modification sites by MS analysis. The amino acid residues at the positions of cysteine 254 and cysteine 492 of RRM1 protein and cysteine 202 of RRM2 protein were identified to be tagged with afatinib.

The three identified sites of RRM1 protein and RRM2 protein were closer to the substrate-binding site in structure than the ATP-binding regulatory site [91], leading to the speculation that afatinib might inhibit the RNR activity via covalent incorporation into the substrate-binding site, thus preventing the entry of substrates. To examine the hypothesis, we performed the in vitro afatinib tagging of RNR under ADP competition. RRM1 protein was treated with 0-10 mM ADP first for 15 min, and then the reaction mixture was added with 10 μM afatinib and incubated for an additional 1 h. The results showed that afatinib labeling to RRM1 protein was decreased in the presence of 10 mM ADP (FIG. 11). The same experiment was also performed on RRM2 protein, and afatinib labeling to RRM2 protein was decreased by ADP in a dose-dependent manner (FIG. 11), suggesting that afatinib-binding site in RRM2 is closer to the substrate-binding site. Next, based on the previous studies that gemcitabine was designed to be a RNR inhibitor covalently binding to the substrate-binding site after its conversion to the diphosphate derivative [92] or not [93], we examined whether gemcitabine can compete with afatinib for the substrate-binding site. As expected, pretreatment of 2.5 mM gemcitabine almost completely blocked the afatinib labeling (FIG. 11C). In order to directly examine the effects of afatinib labeling on RNR enzyme activity, we established an in vitro RNR activity assay using intact cells prepared from rapidly growing PC-9 cells. After membrane disruption by freezing and thawing, permeabilized PC-9 cells in each cultured well were treated with 0-100 nM afatinib for 1 h, and RNR activity was estimated by the amount of dCDP generated following the addition of a reagent mixture containing ATP and CDP for 1 h. Since nucleosides are better resolved and detected than nucleotides in LC-MS analysis [94], the reaction product dCDP was extracted from the reaction solution and treated with alkaline phosphatase. The digested products, deoxycytidine and cytidine, were well separated in LC. Treatment of PC-9 cell lysate in vitro with 10 and 100 nM afatinib potently inhibited the production of dCDP (FIG. 11D). Thus, these results support the notion that afatinib may directly inhibit RNR activity via covalent occupation of substrate-binding site.

Combinational Therapeutic Effect In Vitro and In Vivo of Covalently Bound Inhibitor in Control of Diseases Since sforementioned technologies allow rapid examination of novel targets not known, we show examples to indicate usefulness of the technologies in current disease control. For afatinib in anti-cancer studies, ability of afatinib to combine with gemcitabine to show additional synergistic response can show proof of concept that afatinib is working on additional pathways in addition to EGFR and can be used to control diseases not yet proven.

Six-week old male BALB/c nude mice were maintained under specific pathogen-free conditions. PC-9 cells ($1\times10^6$ cells resuspended in 100 μL Opti-MEM) were inoculated subcutaneously into the right flank per nude mouse. After 14 days, when tumors grew with the volumes of approximate 56-58 $mm^3$ and animals had the weights of approximate 23-24 g, the mice were randomly assigned to four groups: afatinib group (n=10), gemcitabine group (n=10), afatinib+gemcitabine group (n=10), and control group (n=10). Afatinib (10 mg/kg) was administered by oral gavage every day. Intraperitoneal injection was used for gemcitabine for the drug delivery into mice [100 mg/kg in PBS, every week (Day 1 and Day 8)]. Sterile water was administered by oral gavage every day and sterile PBS was given to the mice by intraperitoneal injection every week as control treatment. Body weights and tumor sizes were measured and recorded every 3 days. Tumor volumes were calculated using the following equation: volume (mm3)=length×width2×0.5. After 15-day treatment, the mice were euthanized, and tumor lesions and masses were photographed and weighed. The tumor volumes and masses were statistically calculated and plotted.

To mimic the in vivo afatinib therapeutic conditions, we extended the incubation time of afatinib to 48 h with one replacement of the culture medium containing afatinib at 24 h. Under the prolonged treatment conditions, the protein level of RRM2 was significantly reduced by the treatment of 100 nM and 1 μM of afatinib, while EGFR protein levels were increased upon the treatment with 1 nM to 100 nM afatinib. Therefore, the long-term incubation with afatinib significantly lowers the effective concentration of afatinib against RRM2 in cultured cells. In order to exclude the possibility that inhibition of EGFR by afatinib may cause downregulation of other afatinib targets, we chose the EGFR-null CHO cells [95] to examine the effects of afatinib on the protein levels of RRM1 and RRM2. The long-term incubation of afatinib in CHO cells also leaded to decreasing RRM2 protein levels in a dose-response manner. Like PC-9 cells, RRM1 was relatively resistant to the afatinib treatment in CHO cells. We also found that afatinib also could increase the levels of γ-H2AX in CHO cells at a dose-response manner after 24 h treatment. However, treatment of afatinib at 1 nM to 1 μM did not affect the cell cycle behavior of CHO cells. These results indicate that afatinib can cause the decline of RRM2 protein level and induce DNA damage in cells, which are apparently independent of the EGFR signal pathway. In addition, when the duration of afatinib treatment in PC-9 cells was extended to 72 h with daily replacement of the culture medium containing afatinib, the results further showed that the long-term afatinib treatment could decrease the protein levels of RRM1 and RRM2 and increase the protein levels of EGFR in a dose-response manner in PC-9 cells. The results together indicate that at the therapeutic concentrations (10-100 nM) afatinib mainly cause DNA damage, G1 arrest in cell cycle and growth inhibition, but not cell death of human lung cancer cells.

REFERENCES

1. Tonks N K. Protein tyrosine phosphatases: from genes, to function, to disease. Nat Rev Mol Cell Biol. 2006; 7(11):833-46.

2. Barford D, Flint A J, Tonks N K. Crystal structure of human protein tyrosine phosphatase 1B. Science. 1994; 263(5152):1397-404.
3. Zhang Z Y, Wang Y, Dixon J E. Dissecting the catalytic mechanism of protein-tyrosine phosphatases. Proc Natl Acad Sci USA. 1994; 91(5):1624-7.
4. Lee S R, Kwon K S, Kim S R, Rhee S G. Reversible inactivation of protein-tyrosine phosphatase 1B in A431 cells stimulated with epidermal growth factor. J Biol Chem. 1998; 273(25):15366-72.
5. Meng T C, Fukada T, Tonks N K. Reversible oxidation and inactivation of protein tyrosine phosphatases in vivo. Mol Cell. 2002; 9(2):387-99.
6. Meng T C, Buckley D A, Galic S, Tiganis T, Tonks N K. Regulation of insulin signaling through reversible oxidation of the protein-tyrosine phosphatases TC45 and PTP1B. J Biol Chem. 2004; 279(36):37716-25.
7. Capasso M, Bhamrah M K, Henley T, Boyd R S, Langlais C, Cain K, et al. HVCN1 modulates BCR signal strength via regulation of BCR-dependent generation of reactive oxygen species. Nat Immunol. 2010; 11(3):265-72.
8. Singh D K, Kumar D, Siddiqui Z, Basu S K, Kumar V, Rao K V. The strength of receptor signaling is centrally controlled through a cooperative loop between Ca2+ and an oxidant signal. Cell. 2005; 121(2):281-93.
9. Barrett D M, Black S M, Todor H, Schmidt-Ullrich R K, Dawson K S, Mikkelsen R B. Inhibition of protein-tyrosine phosphatases by mild oxidative stresses is dependent on S-nitrosylation. J Biol Chem. 2005; 280 (15):14453-61.
10. Hsu M F, Meng T C. Enhancement of insulin responsiveness by nitric oxide-mediated inactivation of protein-tyrosine phosphatases. J Biol Chem. 2010; 285 (11):7919-28.
11. Robertson S C, Tynan J, Donoghue D J. RTK mutations and human syndromes: when good receptors turn bad. Trends Genet. 2000; 16(8):368.
12. Hendriks W J, Elson A, Harroch S, Pulido R, Stoker A, den Hertog J. Protein tyrosine phosphatases in health and disease. FEBS J. 2013; 280(2):708-30.
13. Elchebly M, Payette P, Michaliszyn E, Cromlish W, Collins S, Loy A L, et al. Increased insulin sensitivity and obesity resistance in mice lacking the protein tyrosine phosphatase-1B gene. Science. 1999; 283 (5407):1544-8.
14. Klaman L D, Boss O, Peroni O D, Kim J K, Martino J L, Zabolotny J M, et al. Increased energy expenditure, decreased adiposity, and tissue-specific insulin sensitivity in protein-tyrosine phosphatase 1B-deficient mice. Mol Cell Biol. 2000; 20(15):5479-89.
15. Muise A M, Walters T, Wine E, Griffiths A M, Turner D, Duerr R H, et al. Protein-tyrosine phosphatase sigma is associated with ulcerative colitis. Curr Biol. 2007; 17(14):1212-8.
16. Vang T, Miletic A V, Bottini N, Mustelin T. Protein tyrosine phosphatase PTPN22 in human autoimmunity. Autoimmunity. 2007; 40(6):453-61.
17. Fousteri G, Liossis S N, Battaglia M. Roles of the protein tyrosine phosphatase PTPN22 in immunity and autoimmunity. Clin Immunol. 2013; 149(3):556-65.
18. Andersen J N, Mortensen O H, Peters G H, Drake P G, Iversen L F, Olsen O H, et al. Structural and evolutionary relationships among protein tyrosine phosphatase domains. Mol Cell Biol. 2001; 21(21): 7117-36.
19. Martin K R, Narang P, Medina-Franco J L, Meurice N, MacKeigan JP. Integrating virtual and biochemical screening for protein tyrosine phosphatase inhibitor discovery. Methods. 2014; 65(2):219-28.
20. Mestres J, Gregori-Puigjane E, Valverde S, Sole R V. Data completeness—the Achilles heel of drug-target networks. Nat Biotechnol. 2008; 26(9):983-4.
21. Futamura Y, Muroi M, Osada H. Target identification of small molecules based on chemical biology approaches. Mol Biosyst. 2013; 9(5):897-914.
22. Liu S, Zhou B, Yang H, He Y, Jiang Z X, Kumar S, et al. Aryl vinyl sulfonates and sulfones as active site-directed and mechanism-based probes for protein tyrosine phosphatases. J Am Chem Soc. 2008; 130(26): 8251-60
23. Ho W H, Lee D Y, Chang G D. Proteomic identification of a novel hsp90-containing protein-mineral complex which can be induced in cells in response to massive calcium influx. J Proteome Res. 2012; 11(6): 3160-74.
24. Huyer G, Liu S, Kelly J, Moffat J, Payette P, Kennedy B, et al. Mechanism of inhibition of protein-tyrosine phosphatases by vanadate and pervanadate. J Biol Chem. 1997; 272(2):843-51.
25. Liljebris C, Baranczewski P, Bjorkstrand E, Bystrom S, Lundgren B, Tjernberg A, et al. Oxidation of protein tyrosine phosphatases as a pharmaceutical mechanism of action: a study using 4-hydroxy-3,3-dimethyl-2H-benzo[g]indole-2,5(3H)-dione. J Pharmacol Exp Ther. 2004; 309(2):711-9.
26. Lazo J S, Nemoto K, Pestell K E, Cooley K, Southwick E C, Mitchell D A, et al. Identification of a potent and selective pharmacophore for Cdc25 dual specificity phosphatase inhibitors. Mol Pharmacol. 2002; 61(4): 720-8.
27. Messana I, Cabras T, lavarone F, Vincenzoni F, Urbani A, Castagnola M. Unraveling the different proteomic platforms. J Sep Sci. 2013; 36(1):128-39.
28. Weerapana E, Wang C, Simon G M, Richter F, Khare S, Dillon M B, et al. Quantitative reactivity profiling predicts functional cysteines in proteomes. Nature. 2010; 468(7325):790-5.
29. Go Y M, Duong D M, Peng J, Jones D P. Protein Cysteines Map to Functional Networks According to Steady-state Level of Oxidation. J Proteomics Bioinform. 2011; 4(10):196-209.
30. Paulsen C E, Carroll K S. Cysteine-mediated redox signaling: chemistry, biology, and tools for discovery. Chem Rev. 2013; 113(7):4633-79.
31. Winterbourn C C, Hampton M B. Thiol chemistry and specificity in redox signaling. Free Radic Biol Med. 2008; 45(5):549-61.
32. Karplus P A, Schulz G E. Substrate binding and catalysis by glutathione reductase as derived from refined enzyme: substrate crystal structures at 2 A resolution. J Mol Biol. 1989; 210(1):163-80.
33. Ghashghaeinia M, Giustarini D, Koralkova P, Koberle M, Alzoubi K, Bissinger R, et al. Pharmacological targeting of glucose-6-phosphate dehydrogenase in human erythrocytes by Bay 11-7082, parthenolide and dimethyl fumarate. Sci Rep. 2016; 6:28754.
34. Nicholson T B, Chen T, Richard S. The physiological and pathophysiological role of PRMT1-mediated protein arginine methylation. Pharmacol Res. 2009; 60(6): 466-74.
35. Tang J, Kao P N, Herschman H R. Protein-arginine methyltransferase I, the predominant protein-arginine methyltransferase in cells, interacts with and is regulated by interleukin enhancer-binding factor 3. J Biol Chem. 2000; 275(26): 19866-76.

36. Strahl B D, Briggs S D, Brame C J, Caldwell J A, Koh S S, Ma H, et al. Methylation of histone H4 at arginine 3 occurs in vivo and is mediated by the nuclear receptor coactivator PRMT1. Curr Biol. 2001; 11(12):996-1000.

37. Wang H, Huang Z Q, Xia L, Feng Q, Erdjument-Bromage H, Strahl B D, et al. Methylation of histone H4 at arginine 3 facilitating transcriptional activation by nuclear hormone receptor. Science. 2001; 293 (5531):853-7.

38. Cheng D, Yadav N, King R W, Swanson M S, Weinstein E J, Bedford M T. Small molecule regulators of protein arginine methyltransferases. J Biol Chem. 2004; 279(23):23892-9.

39. Dhar S, Vemulapalli V, Patananan A N, Huang G L, Di Lorenzo A, Richard S, et al. Loss of the major Type I arginine methyltransferase PRMT1 causes substrate scavenging by other PRMTs. Sci Rep. 2013; 3:1311.

40. Kim C, Lim Y, Yoo B C, Won N H, Kim S, Kim G. Regulation of post-translational protein arginine methylation during HeLa cell cycle. Biochim Biophys Acta. 2010; 1800(9):977-85.

41. Heinke R, Spannhoff A, Meier R, Trojer P, Bauer I, Jung M, et al. Virtual screening and biological characterization of novel histone arginine methyltransferase PRMT1 inhibitors. ChemMedChem. 2009; 4(1):69-77.

42. Relic B, Charlier E, Deroyer C, Malaise O, Neuville S, Desoroux A, et al. BAY 11-7085 induces glucocorticoid receptor activation and autophagy that collaborate with apoptosis to induce human synovial fibroblast cell death. Oncotarget. 2016; 7(17):23370-82.

43. Berger N, Ben Bassat H, Klein B Y, Laskov R. Cytotoxicity of NF-kappaB inhibitors Bay 11-7085 and caffeic acid phenethyl ester to Ramos and other human B-lymphoma cell lines. Exp Hematol. 2007; 35(10): 1495-509.

44. Johnson D S, Weerapana E, Cravatt B F. Strategies for discovering and derisking covalent, irreversible enzyme inhibitors. Future Med Chem. 2010; 2(6):949-64.

45. Singh J, Petter R C, Baillie T A, Whitty A. The resurgence of covalent drugs. Nat Rev Drug Discov. 2011; 10(4):307-17.

46. Liu Q, Sabnis Y, Zhao Z, Zhang T, Buhrlage S J, Jones L H, et al. Developing irreversible inhibitors of the protein kinase cysteinome. Chem Biol. 2013; 20(2): 146-59.

47. Yang J C, Hirsh V, Schuler M, Yamamoto N, O'Byrne K J, Mok T S, et al. Symptom control and quality of life in LUX-Lung 3: a phase III study of afatinib or cisplatin/pemetrexed in patients with advanced lung adenocarcinoma with EGFR mutations. J Clin Oncol. 2013; 31(27):3342-50.

48. Sequist L V, Yang J C, Yamamoto N, O'Byrne K, Hirsh V, Mok T, et al. Phase III study of afatinib or cisplatin plus pemetrexed in patients with metastatic lung adenocarcinoma with EGFR mutations. J Clin Oncol. 2013; 31(27):3327-34.

49. Dungo R T, Keating G M. Afatinib: first global approval. Drugs. 2013; 73(13):1503-15.

50. Byrd J C, Furman R R, Coutre S E, Flinn I W, Burger J A, Blum K A, et al. Targeting BTK with ibrutinib in relapsed chronic lymphocytic leukemia. N Engl J Med.

51. Wang M L, Rule S, Martin P, Goy A, Auer R, Kahl B S, et al. Targeting BTK with ibrutinib in relapsed or refractory mantle-cell lymphoma. N Engl J Med. 2013; 369(6):507-16.

52. Evans M J, Cravatt B F. Mechanism-based profiling of enzyme families. Chem Rev. 2006; 106(8):3279-301.

53. Cravatt B F, Wright A T, Kozarich J W. Activity-based protein profiling: from enzyme chemistry to proteomic chemistry. Annu Rev Biochem. 2008; 77:383-414.

54. Speers A E, Adam G C, Cravatt B F. Activity-based protein profiling in vivo using a copper(i)-catalyzed azide-alkyne [3+2] cycloaddition. J Am Chem Soc. 2003; 125(16):4686-7.

55. Hang H C, Loureiro J, Spooner E, van der Velden A W, Kim Y M, Pollington A M, et al. Mechanism-based probe for the analysis of cathepsin cysteine proteases in living cells. ACS Chem Biol. 2006; 1(11):713-23.

56. Edgington L E, Berger A B, Blum G, Albrow V E, Paulick M G, Lineberry N, et al. Noninvasive optical imaging of apoptosis by caspase-targeted activity-based probes. Nat Med. 2009; 15(8):967-73.

57. Su Y, Ge J, Zhu B, Zheng Y G, Zhu Q, Yao S Q. Target identification of biologically active small molecules via in situ methods. Curr Opin Chem Biol. 2013; 17(5): 768-75.

58. Yang P Y, Liu K, Ngai M H, Lear M J, Wenk M R, Yao S Q. Activity-based proteome profiling of potential cellular targets of Orlistat—an FDA-approved drug with anti-tumor activities. J Am Chem Soc. 2010; 132(2):656-66.

59. Kumar S, Zhou B, Liang F, Wang W Q, Huang Z, Zhang Z Y. Activity-based probes for protein tyrosine phosphatases. Proc Natl Acad Sci USA. 2004; 101(21): 7943-8.

60. Kumar S, Zhou B, Liang F, Yang H, Wang W Q, Zhang Z Y. Global analysis of protein tyrosine phosphatase activity with ultra-sensitive fluorescent probes. J Proteome Res. 2006; 5(8):1898-905.

61. Pierce J W, Schoenleber R, Jesmok G, Best J, Moore S A, Collins T, et al. Novel inhibitors of cytokine-induced IkappaBalpha phosphorylation and endothelial cell adhesion molecule expression show anti-inflammatory effects in vivo. J Biol Chem. 1997; 272(34): 21096-103.

62. Krishnan N, Bencze G, Cohen P, Tonks N K. The anti-inflammatory compound BAY-11-7082 is a potent inhibitor of protein tyrosine phosphatases. FEBS J.

63. Strickson S, Campbell D G, Emmerich C H, Knebel A, Plater L, Ritorto M S, et al. The anti-inflammatory drug BAY 11-7082 suppresses the MyD88-dependent signalling network by targeting the ubiquitin system. Biochem J. 2013; 451(3):427-37.

64. Gersch M, Kreuzer J, Sieber S A. Electrophilic natural products and their biological targets. Nat Prod Rep. 2012; 29(6):659-82.

65. Citri A, Yarden Y. EGF-ERBB signalling: towards the systems level. Nat Rev Mol Cell Biol. 2006; 7: 505-16. doi: 10.1038/nrm1962.

66. Tao R H, Maruyama I N. All EGF(ErbB) receptors have preformed homo- and heterodimeric structures in living cells. J Cell Sci. 2008; 121: 3207-17. doi: 10.1242/jcs.033399.

67. Mendelsohn J, Baselga J. The EGF receptor family as targets for cancer therapy. Oncogene. 2000; 19: 6550-65. doi: 10.1038/sj.onc.1204082.

68. Barf T, Kaptein A. Irreversible protein kinase inhibitors: balancing the benefits and risks. J Med Chem. 2012; 55: 6243-62. doi: 10.1021/jm3003203.

69. Hirsh V. Afatinib (BIBW 2992) development in non-small-cell lung cancer. Future Oncol. 2011; 7: 817-25. doi: 10.2217/fon.11.62.

70. Li D, Ambrogio L, Shimamura T, Kubo S, Takahashi M, Chirieac L R, Padera R F, Shapiro G I, Baum A, Himmelsbach F, Rettig W J, Meyerson M, Solca F, et al. BIBW2992, an irreversible EGFR/HER2 inhibitor highly effective in preclinical lung cancer models. Oncogene. 2008; 27: 4702-11. doi: 10.1038/onc.2008.109.

71. Solca F, Dahl G, Zoephel A, Bader G, Sanderson M, Klein C, Kraemer O, Himmelsbach F, Haaksma E, Adolf G R. Target binding properties and cellular activity of afatinib (BIBW 2992), an irreversible ErbB family blocker. J Pharmacol Exp Ther. 2012; 343: 342-50. doi: 10.1124/jpet.112.197756.

72. Sequist L V, Yang J C, Yamamoto N, O'Byrne K, Hirsh V, Mok T, Geater S L, Orlov S, Tsai C M, Boyer M, Su W C, Bennouna J, Kato T, et al. Phase III study of afatinib or cisplatin plus pemetrexed in patients with metastatic lung adenocarcinoma with EGFR mutations. J Clin Oncol. 2013; 31: 3327-34. doi: 10.1200/JCO.2012.44.2806.

73. Wu Y L, Zhou C, Hu C P, Feng J, Lu S, Huang Y, Li W, Hou M, Shi J H, Lee K Y, Xu C R, Massey D, Kim M, et al. Afatinib versus cisplatin plus gemcitabine for first-line treatment of Asian patients with advanced non-small-cell lung cancer harbouring EGFR mutations (LUX-Lung 6): an open-label, randomised phase 3 trial. Lancet Oncol. 2014; 15: 213-22. doi: 10.1016/S1470-2045(13)70604-1.

74. Brockstein B E. Management of recurrent head and neck cancer: recent progress and future directions. Drugs. 2011; 71: 1551-9. doi: 10.2165/11592540-000000000-00000.

75. Burtness B, Bourhis J P, Vermorken J B, Harrington K J, Cohen E E. Afatinib versus placebo as adjuvant therapy after chemoradiation in a double-blind, phase III study (LUX-Head & Neck 2) in patients with primary unresected, clinically intermediate-to-high-risk head and neck cancer: study protocol for a randomized controlled trial. Trials. 2014; 15: 469. doi: 10.1186/1745-6215-15-469.

76. Harbeck N, Solca F, Gauler T C. Preclinical and clinical development of afatinib: a focus on breast cancer and squamous cell carcinoma of the head and neck. Future Oncol. 2014; 10: 21-40. doi: 10.2217/fon.13.244.

77. Hurvitz S A, Shatsky R, Harbeck N. Afatinib in the treatment of breast cancer. Expert Opin Investig Drugs. 2014; 23: 1039-47. doi: 10.1517/13543784.2014.924505.

78. Zhang X, Munster P N. New protein kinase inhibitors in breast cancer: afatinib and neratinib. Expert Opin Pharmacother. 2014; 15: 1277-88. doi: 10.1517/14656566.2014.913570.

79. Ahmad M F, Dealwis C G. The structural basis for the allosteric regulation of ribonucleotide reductase. Prog Mol Biol Transl Sci. 2013; 117: 389-410. doi: 10.1016/B978-0-12-386931-9.00014-3.

80. Aye Y, Li M, Long M J, Weiss R S. Ribonucleotide reductase and cancer: biological mechanisms and targeted therapies. Oncogene. 2015; 34: 2011-21. doi: 10.1038/onc.2014.155.

81. Souglakos J, Boukovinas I, Taron M, Mendez P, Mavroudis D, Tripaki M, Hatzidaki D, Koutsopoulos A, Stathopoulos E, Georgoulias V, Rosell R. Ribonucleotide reductase subunits M1 and M2 mRNA expression levels and clinical outcome of lung adenocarcinoma patients treated with docetaxel/gemcitabine. Br J Cancer. 2008; 98: 1710-5. doi: 10.1038/sj.bjc.6604344.

82. Goan Y G, Zhou B, Hu E, Mi S, Yen Y. Overexpression of ribonucleotide reductase as a mechanism of resistance to 2,2-difluorodeoxycytidine in the human KB cancer cell line. Cancer Res. 1999; 59: 4204-7. doi:

83. Davidson J D, Ma L, Flagella M, Geeganage S, Gelbert L M, Slapak C A. An increase in the expression of ribonucleotide reductase large subunit 1 is associated with gemcitabine resistance in non-small cell lung cancer cell lines. Cancer Res. 2004; 64: 3761-6. doi: 10.1158/0008-5472.CAN-03-3363.

84. Liu Q, Kirubakaran S, Hur W, Niepel M, Westover K, Thoreen C C, Wang J, Ni J, Patricelli M P, Vogel K, Riddle S, Waller D L, Traynor R, et al. Kinome-wide selectivity profiling of ATP-competitive mammalian target of rapamycin (mTOR) inhibitors and characterization of their binding kinetics. J Biol Chem. 2012; 287: 9742-52. doi: 10.1074/jbc.M111.304485.

85. Wu H, Wang W, Liu F, Weisberg E L, Tian B, Chen Y, Li B, Wang A, Wang B, Zhao Z, McMillin D W, Hu C, Li H, et al. Discovery of a potent, covalent BTK inhibitor for B-cell lymphoma. ACS Chem Biol. 2014; 9: 1086-91. doi: 10.1021/cb4008524.

86. Mestres J, Gregori-Puigjane E, Valverde S, Sole R V. Data completeness—the Achilles heel of drug-target networks. Nat Biotechnol. 2008; 26: 983-4. doi: 10.1038/nbt0908-983.

87. Futamura Y, Muroi M, Osada H. Target identification of small molecules based on chemical biology approaches. Mol Biosyst. 2013; 9: 897-914. doi: 10.1039/c2mb25468a.

88. Adachi J, Kishida M, Watanabe S, Hashimoto Y, Fukamizu K, Tomonaga T. Proteome-wide discovery of unknown ATP-binding proteins and kinase inhibitor target proteins using an ATP probe. J Proteome Res. 2014; 13: 5461-70. doi: 10.1021/pr500845u.

89. Wang S Q, Liu S T, Zhao B X, Yang F H, Wang Y T, Liang Q Y, Sun Y B, Liu Y, Song Z H, Cai Y, Li G F. Afatinib reverses multidrug resistance in ovarian cancer via dually inhibiting ATP binding cassette subfamily B member 1. Oncotarget. 2015; 6: 26142-60. doi: 10.18632/oncotarget.4536.

90. Hsieh Y Y, Chou C J, Lo H L, Yang P M. Repositioning of a cyclin-dependent kinase inhibitor GW8510 as a ribonucleotide reductase M2 inhibitor to treat human colorectal cancer. Cell Death Discov. 2016; 2: 16027. doi: 10.1038/cddiscovery.2016.27.

91. Kolberg M, Strand K R, Graff P, Andersson K K. Structure, function, and mechanism of ribonucleotide reductases. Biochim Biophys Acta. 2004; 1699: 1-34. doi: 10.1016/j.bbapap.2004.02.007.

92. Heinemann V, Xu Y Z, Chubb S, Sen A, Hertel L W, Grindey G B, Plunkett W. Inhibition of ribonucleotide reduction in CCRF-CEM cells by 2',2'-difluorodeoxycytidine. Mol Pharmacol. 1990; 38: 567-72. doi:

93. Cory A H, Hertel L W, Kroin J S, Cory J G. Effects of 2',2'-difluorodeoxycytidine (Gemcitabine) on wild type and variant mouse leukemia L1210 cells. Oncol Res. 1993; 5: 59-63. doi:

94. Pomerantz S C, McCloskey J A. Analysis of RNA hydrolyzates by liquid chromatography-mass spectrometry. Methods Enzymol. 1990; 193: 796-824. doi:

95. Ahsan A, Hiniker S M, Davis M A, Lawrence T S, Nyati M K. Role of cell cycle in epidermal growth factor receptor inhibitor-mediated radiosensitization. Cancer Res. 2009; 69: 5108-14. doi: 10.1158/0008-5472.CAN-09-0466.

96. Jones S M, Kazlauskas A. Growth factor-dependent signaling and cell cycle progression. Chem Rev. 2001; 101: 2413-23. doi:

97. Liao G, Wang Z, Zhang N, Dong P. Dominant negative epidermal growth factor receptor inhibits growth of human gastric cancer cells by inducing cell cycle arrest and apoptosis. Cancer Biother Radiopharm. 2013; 28: 450-8. doi: 10.1089/cbr.2012.1399.

98. Peng D, Fan Z, Lu Y, DeBlasio T, Scher H, Mendelsohn J. Anti-epidermal growth factor receptor monoclonal antibody 225 up-regulates p27KIP1 and induces G1 arrest in prostatic cancer cell line DU145. Cancer Res. 1996; 56: 3666-9. doi:

99. Wu X, Fan Z, Masui H, Rosen N, Mendelsohn J. Apoptosis induced by an anti-epidermal growth factor receptor monoclonal antibody in a human colorectal carcinoma cell line and its delay by insulin. J Clin Invest. 1995; 95: 1897-905. doi: 10.1172/JC1117871.

100. Campiglio M, Locatelli A, Olgiati C, Normanno N, Somenzi G, Vigano L, Fumagalli M, Menard S, Gianni L. Inhibition of proliferation and induction of apoptosis in breast cancer cells by the epidermal growth factor receptor (EGFR) tyrosine kinase inhibitor ZD1839 ('Iressa') is independent of EGFR expression level. J Cell Physiol. 2004; 198: 259-68. doi: 10.1002/jcp.10411.

101. Chinnaiyan P, Huang S, Vallabhaneni G, Armstrong E, Varambally S, Tomlins S A, Chinnaiyan A M, Harari P M. Mechanisms of enhanced radiation response following epidermal growth factor receptor signaling inhibition by erlotinib (Tarceva). Cancer Res. 2005; 65: 3328-35. doi: 10.1158/0008-5472.CAN-04-3547.

102. Shintani S, Li C, Mihara M, Yano J, Terakado N, Nakashiro K, Hamakawa H. Gefitinib ('Iressa', ZD1839), an epidermal growth factor receptor tyrosine kinase inhibitor, up-regulates p27KIP1 and induces G1 arrest in oral squamous cell carcinoma cell lines. Oral Oncol. 2004; 40: 43-51. doi:

103. Zhang M, Wang J, Yao R, Wang L. Small interfering RNA (siRNA)-mediated silencing of the M2 subunit of ribonucleotide reductase: a novel therapeutic strategy in ovarian cancer. Int J Gynecol Cancer. 2013; 23: 659-66. doi: 10.1097/IGC.0b013e318287e2b3.

104. Tomas A, Futter C E, Eden E R. EGF receptor trafficking: consequences for signaling and cancer. Trends Cell Biol. 2014; 24: 26-34. doi: 10.1016/j.tcb.2013.11.002.

105. Paez J G, Janne P A, Lee J C, Tracy S, Greulich H, Gabriel S, Herman P, Kaye F J, Lindeman N, Boggon T J, Naoki K, Sasaki H, Fujii Y, et al. EGFR mutations in lung cancer: correlation with clinical response to gefitinib therapy. Science. 2004; 304: 1497-500. doi: 10.1126/science.1099314.

106. Lynch T J, Bell D W, Sordella R, Gurubhagavatula S, Okimoto R A, Brannigan B W, Harris P L, Haserlat S M, Supko J G, Haluska F G, Louis D N, Christiani D C, Settleman J, et al. Activating mutations in the epidermal growth factor receptor underlying responsiveness of non-small-cell lung cancer to gefitinib. N Engl J Med. 2004; 350: 2129-39. doi: 10.1056/NEJMoa040938.

107. Pao W, Miller V, Zakowski M, Doherty J, Politi K, Sarkaria I, Singh B, Heelan R, Rusch V, Fulton L, Mardis E, Kupfer D, Wilson R, et al. EGF receptor gene mutations are common in lung cancers from "never smokers" and are associated with sensitivity of tumors to gefitinib and erlotinib. Proc Natl Acad Sci USA. 2004; 101: 13306-11. doi: 10.1073/pnas.0405220101.

108. Yang J C, Wu Y L, Schuler M, Sebastian M, Popat S, Yamamoto N, Zhou C, Hu C P, O'Byrne K, Feng J, Lu S, Huang Y, Geater S L, et al. Afatinib versus cisplatin-based chemotherapy for EGFR mutation-positive lung adenocarcinoma (LUX-Lung 3 and LUX-Lung 6): analysis of overall survival data from two randomised, phase 3 trials. Lancet Oncol. 2015; 16: 141-51. doi: 10.1016/S1470-2045(14)71173-8.

109. Yap T A, Vidal L, Adam J, Stephens P, Spicer J, Shaw H, Ang J, Temple G, Bell S, Shahidi M, Uttenreuther-Fischer M, Stopfer P, Futreal A, et al. Phase I trial of the irreversible EGFR and HER2 kinase inhibitor BIBW 2992 in patients with advanced solid tumors. J Clin Oncol. 2010; 28: 3965-72. doi: 10.1200/JCO.2009.26.7278.

110. Wu S G, Liu Y N, Tsai M F, Chang Y L, Yu C J, Yang P C, Yang J C, Wen Y F, Shih J Y. The mechanism of acquired resistance to irreversible EGFR tyrosine kinase inhibitor-afatinib in lung adenocarcinoma patients. Oncotarget. 2016; 7: 12404-13. doi: 10.18632/oncotarget.7189.

111. Regales L, Gong Y, Shen R, de Stanchina E, Vivanco I, Goel A, Koutcher J A, Spassova M, Ouerfelli O, Mellinghoff I K, Zakowski M F, Politi K A, Pao W. Dual targeting of EGFR can overcome a major drug resistance mutation in mouse models of EGFR mutant lung cancer. J Clin Invest. 2009; 119: 3000-10. doi: 10.1172/JC138746.

112. Janjigian Y Y, Smit E F, Groen H J, Horn L, Gettinger S, Camidge D R, Riely G J, Wang B, Fu Y, Chand V K, Miller V A, Pao W. Dual inhibition of EGFR with afatinib and cetuximab in kinase inhibitor-resistant EGFR-mutant lung cancer with and without T790M mutations. Cancer Discov. 2014; 4: 1036-45. doi: 10.1158/2159-8290.CD-14-0326.

113. Chao T T, Wang C Y, Chen Y L, Lai C C, Chang F Y, Tsai Y T, Chao C H, Shiau C W, Huang Y C, Yu C J, Chen K F. Afatinib induces apoptosis in NSCLC without EGFR mutation through Elk-1-mediated suppression of CIP2A. Oncotarget. 2015; 6: 2164-79. doi: 10.18632/oncotarget.2941.

114. Wang D, Johnson A D, Papp A C, Kroetz D L, Sadee W. Multidrug resistance polypeptide 1 (MDR1, ABCB1) variant 3435C>T affects mRNA stability. Pharmacogenet Genomics. 2005; 15: 693-704. doi:

115. Wang X K, To K K, Huang L Y, Xu J H, Yang K, Wang F, Huang Z C, Ye S, Fu L W. Afatinib circumvents multidrug resistance via dually inhibiting ATP binding cassette subfamily G member 2 in vitro and in vivo. Oncotarget. 2014; 5: 11971-85. doi: 10.18632/oncotarget.2647.

116. Huang P, Chubb S, Hertel L W, Grindey G B, Plunkett W. Action of 2',2'-difluorodeoxycytidine on DNA synthesis. Cancer Res. 1991; 51: 6110-7. doi:

117. Crescenzi E, Chiaviello A, Canti G, Reddi E, Veneziani B M, Palumbo G. Low doses of cisplatin or gemcitabine plus Photofrin/photodynamic therapy:

Disjointed cell cycle phase-related activity accounts for synergistic outcome in metastatic non-small cell lung cancer cells (H1299). Mol Cancer Ther. 2006; 5: 776-85. doi: 10.1158/1535-7163.MCT-05-0425.

118. Tolis C, Peters G J, Ferreira C G, Pinedo H M, Giaccone G. Cell cycle disturbances and apoptosis induced by topotecan and gemcitabine on human lung cancer cell lines. Eur J Cancer. 1999; 35: 796-807. doi:

What is claimed is:

1. A method for a detection of novel binding proteins of a pharmaceutical chemical compound or its derivatives performed with lysates from cultured human cells, comprising following steps:

(a) generating a detection agent raised by a complex of the pharmaceutical chemical compound conjugated with a protein carrier, wherein the pharmaceutical chemical compound is protein tyrosine kinase inhibitor or protein tyrosine phosphatase inhibitor; wherein the protein tyrosine kinase inhibitor is afatinib, or its derivatives erlotinib or gefitinib; and wherein the protein tyrosine phosphatase inhibitor is phenyl vinyl sulfone (PVS), or its derivatives phenyl vinyl sulfonate (PVSN) or Bay 11-7082; the detection agent is antiserum, single-chain variable fragment binding protein, monoclonal antibody in any immunoglobulin format, or a combination thereof, which is against the pharmaceutical chemical compound;

(b) generating cellular lysates after the pharmaceutical chemical compound treatment from cultured human cells;

(c) executing an immunoprecipitation performed with the cellular lysates and the detection agent to immunoprecipitate a complex of the pharmaceutical chemical compound and its target binding proteins;

(d) executing a proteomic analysis to identify the target binding proteins of the pharmaceutical chemical compound.

2. The method of claim 1, wherein the protein carrier is keyhole limpet Hemocyanin, ovalbumin or bovine serum albumin.

3. The method of claim 1, wherein ribonucleotide reductase (RNR) is one of the target binding proteins of the pharmaceutical chemical compound.

4. The method of claim 1, wherein nuclear factor of kappa B (NFKB) is one of the target binding proteins of the pharmaceutical chemical compound.

5. The method of claim 1, wherein protein arginine methyltransferase 1 (PRMT1) is one of the target binding proteins of the pharmaceutical chemical compound.

* * * * *